United States Patent [19]

Shibata et al.

[11] Patent Number: 4,623,008
[45] Date of Patent: Nov. 18, 1986

[54] AUTOMATIC DISPENSING SYSTEM

[75] Inventors: Shinich Shibata; Takashi Ito, both of Saitama, Japan

[73] Assignee: Sakata Shokai, Ltd., Osaka, Japan

[21] Appl. No.: 639,478

[22] Filed: Aug. 10, 1984

[30] Foreign Application Priority Data

Aug. 12, 1983 [JP] Japan .................................. 58-147352
Aug. 24, 1983 [JP] Japan .................................. 58-154272

[51] Int. Cl.$^4$ .............................................. B65B 3/04
[52] U.S. Cl. ........................................ 141/89; 141/98; 141/100; 141/250; 73/864.01; 137/88; 222/52; 422/100
[58] Field of Search ..................................... 141/1–12, 141/37–66, 85–92, 100–110, 98, 129–191, 250–284; 137/3, 88, 93; 73/864–864.25; 422/100; 222/52–69

[56] References Cited

U.S. PATENT DOCUMENTS

| 2,978,951 | 4/1961 | Christie | 137/3 |
| 4,046,287 | 9/1977 | Hoekstra et al. | 222/16 |
| 4,314,653 | 2/1982 | Sindoni | 222/41 |

FOREIGN PATENT DOCUMENTS

| 122068 | 3/1980 | Japan . |
| 56-74715 | 6/1981 | Japan . |
| 159342 | 12/1981 | Japan . |
| 66171 | 4/1982 | Japan . |

*Primary Examiner*—Houston S. Bell, Jr.
*Attorney, Agent, or Firm*—Wenderoth Lind & Ponack

[57] ABSTRACT

A system for automatically dispensing stock solutions is disclosed, comprising a dispenser, pipette keeping and washing units and a control unit. The respective pipette keeping and washing units have different types of pipettes. First, the control unit selects the most appropriate pipette according to the type and amount of mixture of stock solutions to be prepared. The dispenser then receives the selected pipette from the corresponding pipette keeping and washing unit and is detachably fitted with the appropriate pipette to feed a predetermined amount of stock solution into a receptacle by manipulating the pipette. Having finished dispensing, the dispenser transfers the used pipette back to the corresponding pipette keeping and washing unit. On completion of the transfer, the control unit causes the pipette keeping and washing unit to wash the transferred pipette. In the meanwhile, the control unit selects another pipette and the dispenser dispenses stock solution in the receptacles by using the newly selected pipette. Thus, the processing of dispensing stock solutions to the receptacles can be efficiently effected by saving the time loss which would be caused by interruptions for cleaning the pipette.

Further a secondary feature of the invention includes an apparatus for automatically preparing stock solutions thereby saving the time and labor which would be required in manually preparing stock solutions.

18 Claims, 21 Drawing Figures

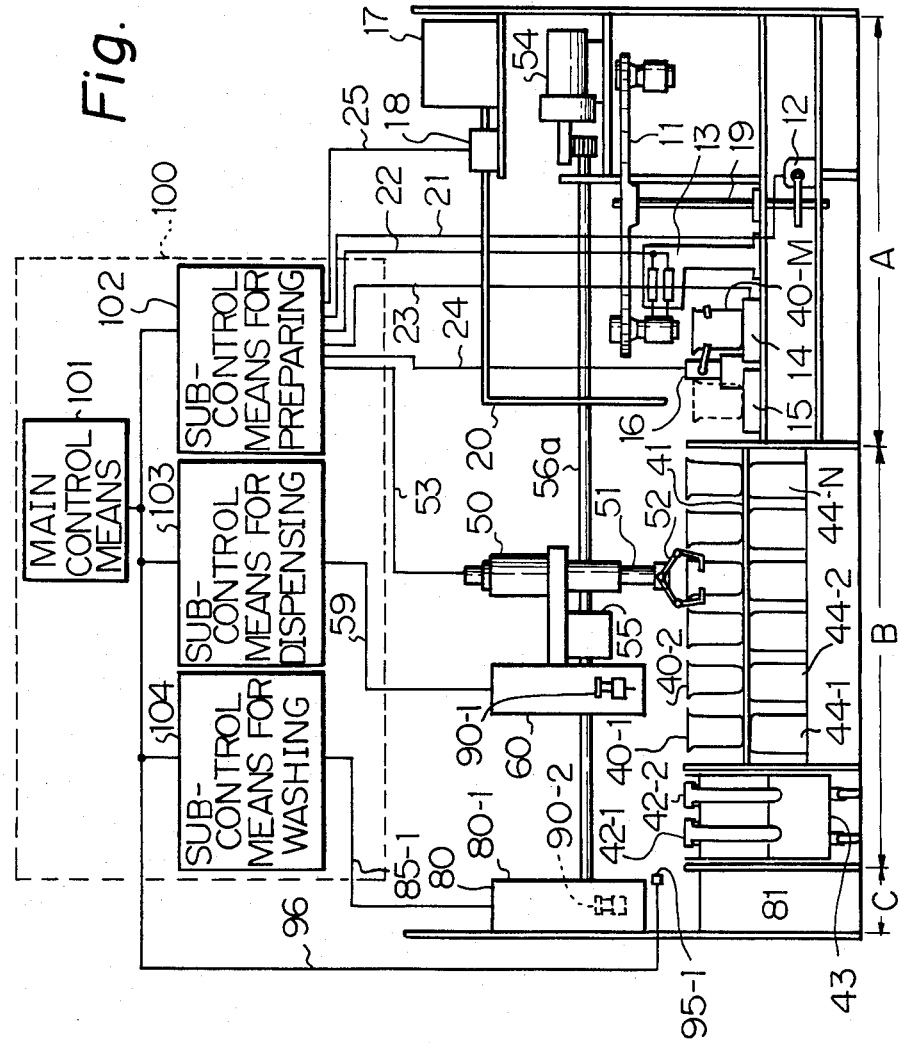

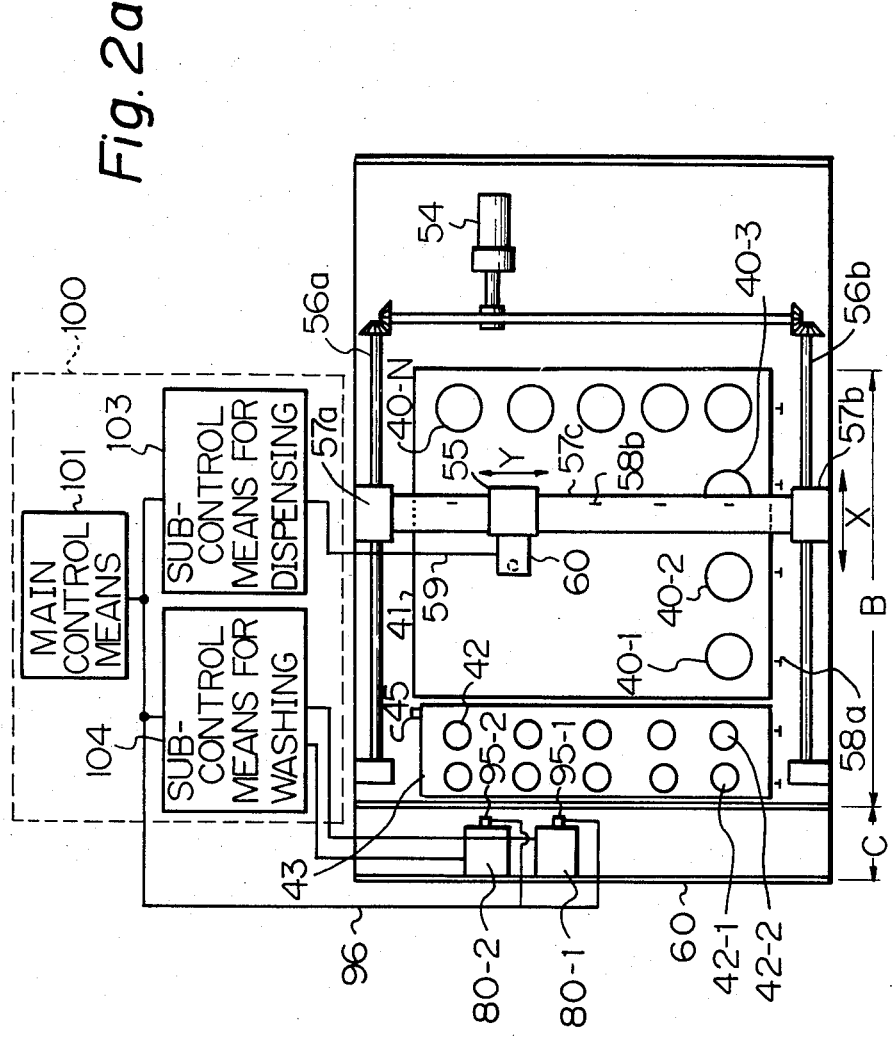

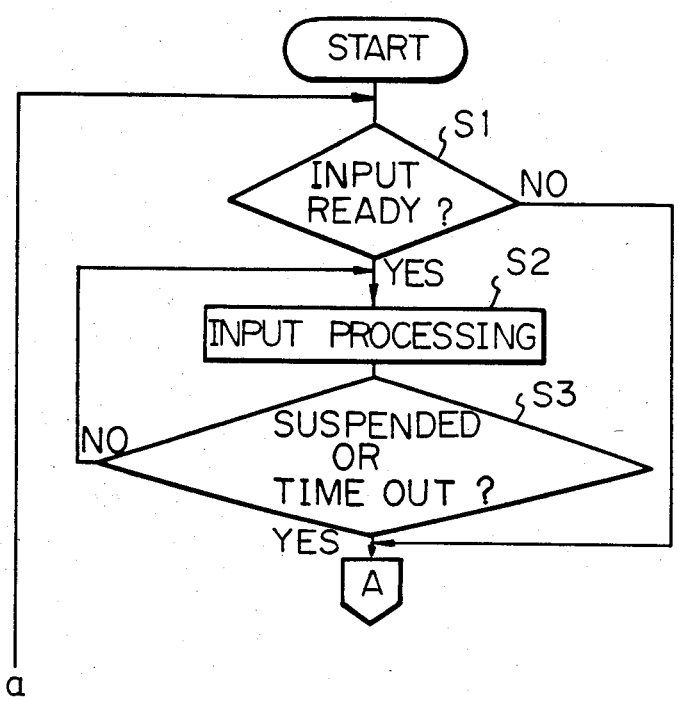
Fig. 6a1.

Fig. 6b1.
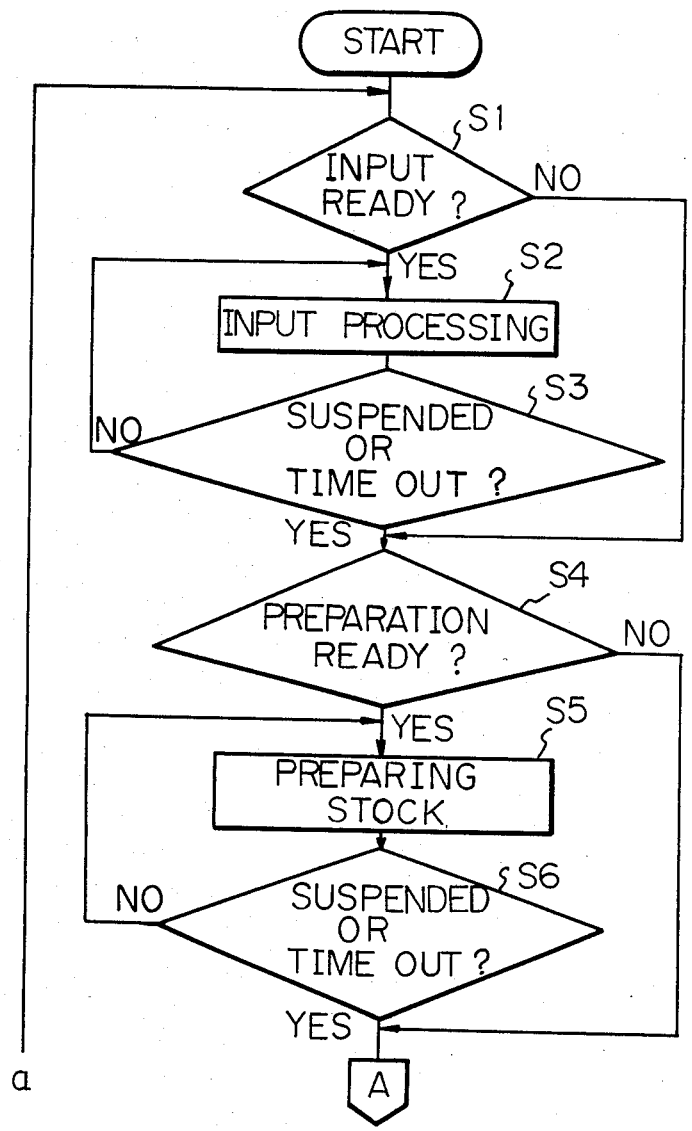

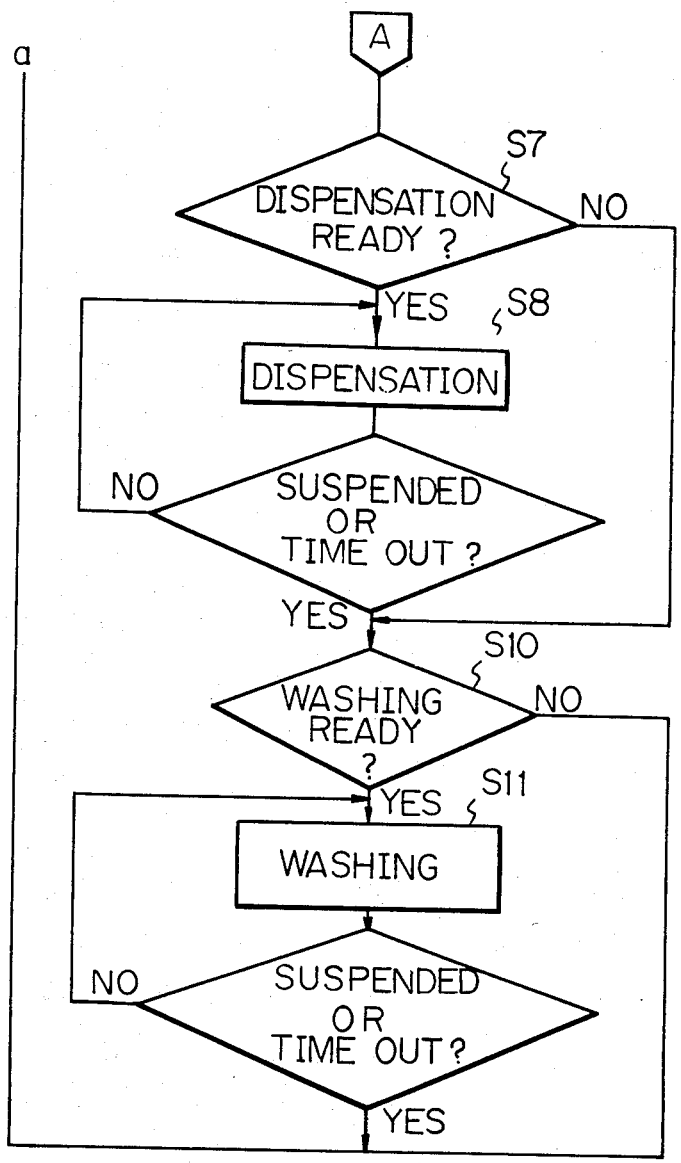
Fig. 6b2.

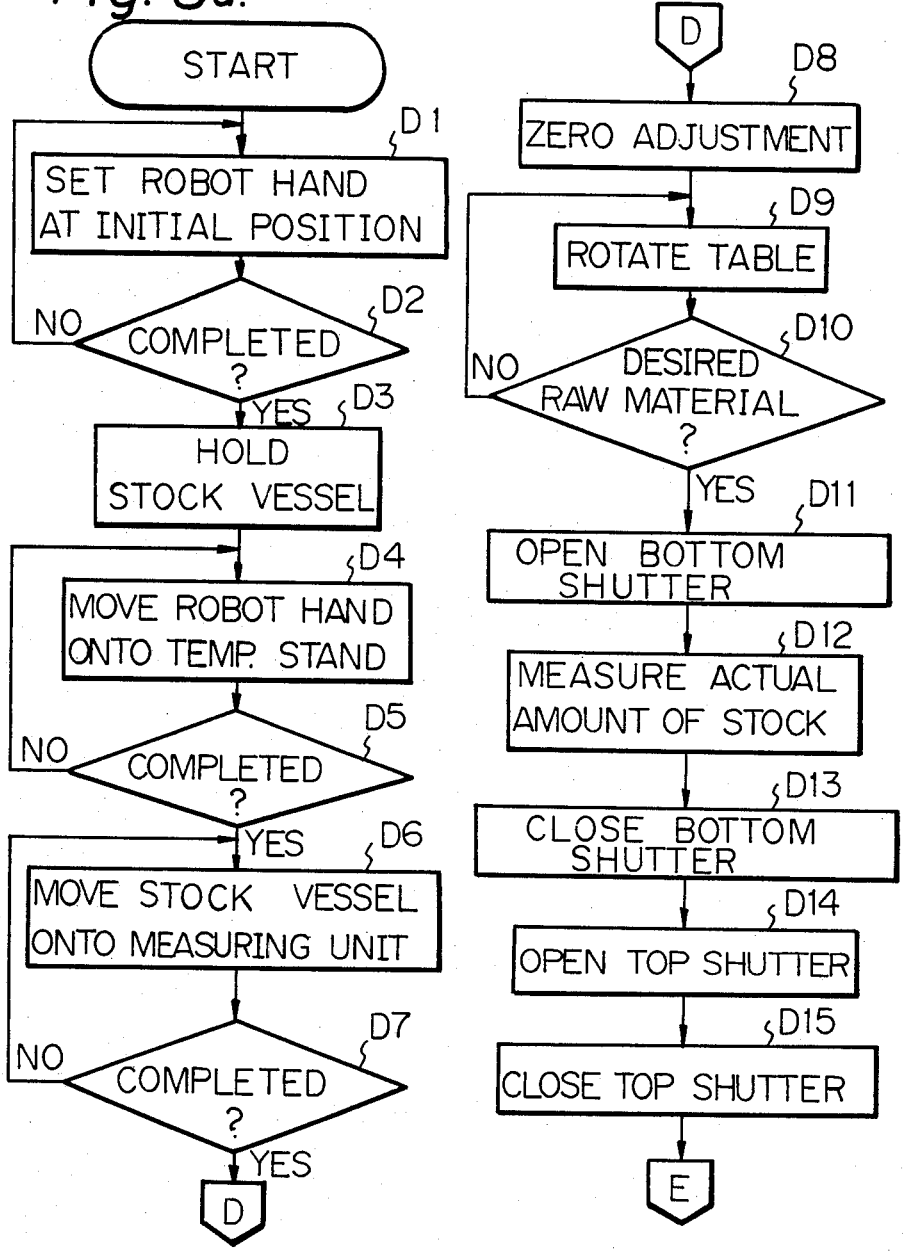

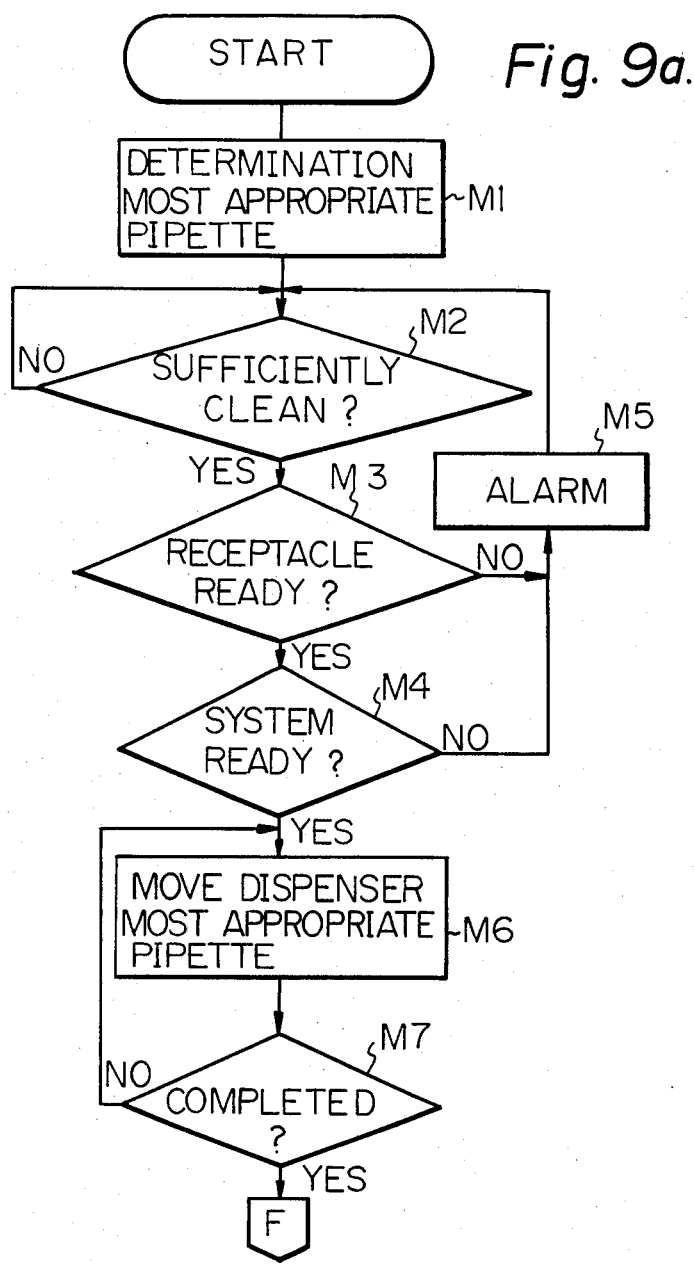

AUTOMATIC DISPENSING SYSTEM

BACKGROUND OF THE INVENTION

1. Field of the Invention

The present invention relates to an automatic dispensing system for preparing various kinds of solvent mixture and more particularly to a system for automatically preparing various kinds of dyeing solvent by mixing mother dyeing solutions.

While the preferred embodiment of the present invention is directed to a system for automatic preparation of dyeing solvent, it should be understood that the present invention is applicable to any type of system that is intended for mixing stocks into the desired solvent mixture.

2. Prior Art

Systems have been developed which use a computer for automatically controlling the preparation of a solvent mixture in various fields such as chemical analysis and chemical testing, as well as color matching of dyeing solutions, paints and inks.

Japanese Patent Public Disclosure No. 122068/1980 shows an automatic dispensing system for preparing a dyeing solution comprising tanks of various stock solutions, each of which is connected to a receptacle through a liquid channel such as a pipe, with a dispenser being provided part way along each liquid channel. Commands from the computer control the operation of each dispenser so that the desired flow of each stock solution is supplied to the receptacle.

Japanese Patent Public Disclosure No. 159342/1981 shows an automatic dispensing system for preparing a dyeing solution, wherein the solvent coming from the pipe and received by a receptacle is detected by a sensor, and a valve on the effluent pipe connected to the stock solution is controlled by a computer. However, these two systems have the following defects:

(1) The system configuration is complex since different stock solutions must be connected to the receiving vessel through respective pipes, and dispensers or valves capable of flow control must be provided for each pipe of the feed. The greater the number of types of stock solution needed, the more complex the system configuration becomes;

(2) The feed material adheres to the inner wall of the pipe and may cause clogging. Once such clogging occurs, it is very difficult to remove by washing; and (3) A viscous stock solution involves difficulty in terms of its conveyance through thin pipes and exact metering.

Japanese Patent Public Disclosure No. 66171/1982 shows an automatic dispensing apparatus for preparing a dyeing solution comprising a rotary table and a plurality of dispensers fixedly positioned around the table. The table consists of two stages that rotate relative to each other and each of which has a stock container and a receptacle. The operation of the rotary table in association with the dispensers is controlled by a computer. This system is defective in that the number of stock containers and receptacles that can be mounted on the rotary table is limited because of the necessity for using a relatively low-power motor.

Japanese Patent Public Disclosure No. 122068/1980 also shows an automatic dispensing system which has a movable dispenser, rather than piping, between a plurality of stock tanks and a receiving tank. In operation, the dispenser is moved to a desired stock tank from which a predetermined amount of stock solution is drawn; the dispenser is then moved to the receiving tank into which the stock solution is dispensed. This type of apparatus is free from the problems associated with the use of piping, but it still has the following defects. First, the pipette must be cleaned before a different type of stock solution can be sampled, and this causes an unavoidable interruption in the sample preparing operation. As a further disadvantage, the dispenser uses a single pipette for drawing and dispensing different types of stock solution, so if the amount of the stock solution to be drawn is greater that the capacity of the pipette, several drawings of the stock solution are necessary. If, on the other hand, a predetermined amount of the stock solution to be drawn is considerably smaller than the capacity of the pipette, a precise metering will become difficult.

All of the conventional systems shown above have one common problem; that is, they are not adapted to completely automated dispensing operations because when the initial supply of stock solution is consumed by a dispensing operation, subsequent dispensing operations are impossible without replenishing the stock solution manually.

The present invention has been accomplished to eliminate these problems of the conventional systems.

OBJECT OF THE INVENTION

Accordingly, it is an object of the present invention to provide an automatic dispensing system in which the most appropriate pipette for dispensing stock solution to mixture receptacles to prepare solvent mixtures therein can be selected from a plurality of pipettes having various capacities according to the desired accuracy of metering stock solution and with the desired quantity of stock solution to be dispensed to the receptacles and in which a pipette stained in the dispensation of the stock solution to the receptacles process can be cleaned while the other pipettes are being used for dispensing stock solution to the receptacles. Hereinafter, the process of dispensing stock solutions to mixture receptacles to prepare solvent mixtures will be referred to simply as "the dispensing process".

It is a further object of the present invention to provide an automatic dispensing system adopted subsystem for automatically making various stock solutions to be used for preparing solvent mixtures.

It is yet another object of the present invention to provide an automatic dispensing system in which the processes of stock solution preparation, of dispensing stock solution to mixture receptacles and of washing pipettes can be simultaneously performed in parallel with each other whereby the process of dispensing stock solutions to mixture receptacles can be efficiently effected without interruption for the purpose of cleaning a pipette used in the dispensing process.

SUMMARY OF THE INVENTION

To achieve the foregoing objects and in accordance with a first aspect of the present invention, an automatic dispensing system is provided which includes means for supplying a plurality of pipettes which are manipulatable for inspiring (taking in) stock solutions from stock vessels and for discharging the stock solutions into mixture receptacles; dispensing means including manipulating means having a select one of said plurality of pipettes means detachably attached therewith, for manipulating the selected pipette to take in from the stock vessels and discharge (dispense) into the receptacles the stock solutions; pipette washing means for washing the pipette used by said dispensing means; means for transferring the selected pipette to the manipulating means and for transferring the pipette from the manipulating means to the washing means; and control means for selecting pipette to be provided to said manipulating means and for controlling said manipulating means, transferring means and pipette washing means whereby the process of dispensing stock solutions with a pipette can be efficiently effected simultaneously with washing of previously used pipette with a saving of any time loss due to the interruptions of the dispensing process which would be necessary if the process involved waiting for completion of the washing of a pipette.

In accordance with another aspect of the invention, an automatic stock solution preparing and dispensing system is provided which includes the above elements and in addition stock solution preparing and keeping means for making stock solutions in the stock vessels and and for automatically controlling preparation of said stock solutions by the preparing and keeping means, simultaneously with control of the dispensing means and the pipette washing means whereby the process of dispensing stock solutions can be efficiently effected substantially without time loss due to interruptions for washing the pipette and for preparing stock solutions.

BRIEF DESCRIPTION OF THE DRAWINGS

These and other objects and many of the attendant advantages of the present invention will be readily appreciated as the same becomes better understood by reference to the following detailed description when considered in connection with the accompanying drawings in which:

FIG. 1b is a front view of an automatic stock preparing and dispensing system in accordance with the present invention;

FIG. 2a is a plan view of the automatic dispensing system shown in FIG. 1a;

FIG. 5a is a block schematic diagram showing a control subsystem of the automatic dispensing system shown in FIG. 1a;

FIGS. 6a1 and 6a2 provide a flow chart of a main program for controlling the operation of the automatic dispensing system shown in FIG. 1a;

FIGS. 6b1 and 6b2 provide a flow chart of a main program for controlling the operation of the automatic stock preparing and dispensing system shown in FIG. 1b;

FIG. 7a is a flow chart of a subprogram for inputting data information into the automatic dispensing system shown in FIG. 1a;

FIGS. 8a and 8b provide a flow chart of a subprogram for controlling the stock preparing process;

FIGS. 9a, 9b and 9c provide a flow chart of a subprogram for controlling the dispensing process.

DETAILED DESCRIPTION OF THE PREFERRED EMBODIMENTS

Overall System

Figure 1A:
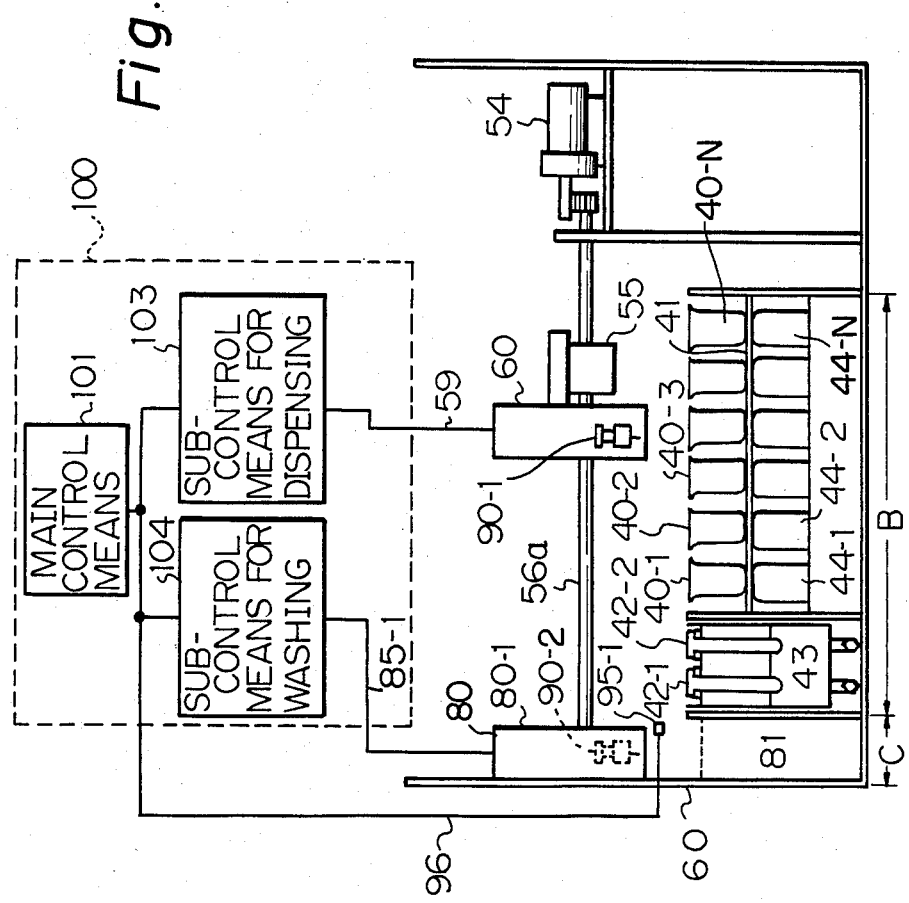
FIG. 1a is a front view of an automatic dispensing system in accordance with the present invention.

Referring now to the drawings wherein like reference characters designate corresponding parts throughout the several views, FIGS. 1a and 2a show the overall front and plan views of an automatic dispensing system embodying the present invention, respectively. In these drawings, reference character B indicates a dispensing subsystem in which desired solvent mixture is prepared in a receptacle by mixing required amounts of stock solutions therein.

Further, reference character C designates a pipette keeping and washing subsystem in which pipettes are washed and kept or held while not being used for dispensing stock solutions to receptacles.

Figure 5A:
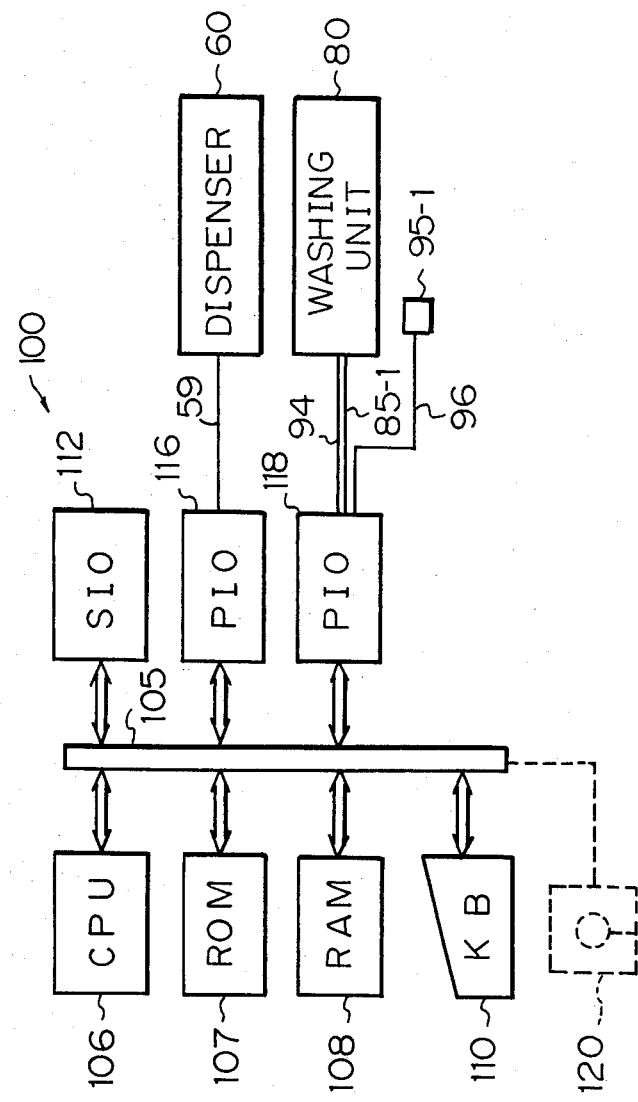

Reference numeral 100 designates a control subsystem including a computer which issues commands for controlling the operations of the above described subsystems. For the sake of simplicity of description, the functional structure of the control subsystem is shown in FIGS. 1a and 2a as being composed of three functional components, i.e., subcontrolling means 103 for the dispensing subsystem, subcontrolling means 104 for the pipette keeping and washing subsystem and main control means 101 for managing the two above described means 103 and 104. The hardware configuration of the control subsystem of this embodiment is shown in FIG. 5a and will be described in detail below, with reference to FIG. 5a.

Dispensing Subsystem

Referring back to FIGS. 1a and 2a, a plurality of stock vessels 40-1, 40-2, . . . , 40-N are disposed in so-called matrix-like configuration on a table 41 at predetermined locations. Various kinds of stock solution with different types, colors, concentrations and so on are put in the vessels, each of which is address-numbered. Beneath the table 41, stirring apparatuses 44-1, 44-2, . . . , 44-N are provided at the positions corresponding to (aligned with) those above which the vessels are placed. These stirrers may be replaced with other instruments such as heating apparatuses according to circumstances.

As shown in FIG. 2a, a plurality of openings or holes are made in so-called matrix-like configuration in a receptacle rest 43 which may be a truck, a bogie or the like. Each receptacle 42 is detachably fitted into the corresponding one of the openings located at predetermined locations which are address-numbered respectively. In this embodiment, the rest 43 is arranged to be taken out from the automatic dispensing system in the upwardly vertical direction as viewed in FIG. 1a, i.e. in the downward direction as viewed in FIG. 2a, on those occasions when all the receptacles are filled up with various solvent mixtures. After all the receptacles have been replaced with empty ones, the rest 43 is again set back into position in the dispensing subsystem. At that time, a sensor 45 shown in FIG. 2a detects normal setting of the rest 43 in the dispensing system.

Detection signals issued from the sensor 45 are sent to the control subsystem 100 through a line (not shown).

A dispenser 60 is equipped with a pipette 90-1 (see FIG. 4) selected from the ones which are kept on pipette keeping or supplying units 80 as will be described in detail afterwards. The keeping units 80 thus serve as a supply for the pipettes provided to the dispenser 60. The dispenser 60 draws a predetermined amount of stock solution from a selected one of the stock vessels 40-1, 40-2, ... 40-N into the pipette 90-1 thereof by manipulating the pipette, and then pours (discharges) a prescribed amount of the stock solution into a preassigned receptacle 42. Such operation of the dispenser is controlled by commands sent out from the subcontrolling means 103 through a line 59.

The dispenser 60 is fixedly fitted to a sliding unit 55 which is operative to slide on a sliding rail 57c in the Y-direction denoted by arrow heads in FIG. 2a. Further, the sliding rail 57c has end portions 57a and 57b which are internally geared with threaded guide shafts 56a and 56b, respectively, and is moved in the X-direction by the driving force of a drive unit 54 by way of the guide shafts 56a and 56b. The sliding unit 55 slides on the upper surface of the rail 57c by rotating wheels (not shown) whose shaft of rotation is connected to a motor (also not shown) enclosed therein. The dispenser 60 can carry any pipettes between the dispensing subsystem B and the pipette keeping units in the subsystem C. Further, the current positions of the dispenser 60 are detected by sensors 58a for detecting movement in the X-direction and sensors 58b for detecting movement in the Y-direction, from both of which sensors detection signals are sent to the control subsystem 100 through a line (not shown).

Pipette Keeping and Washing Subsystem

Figure 2B:
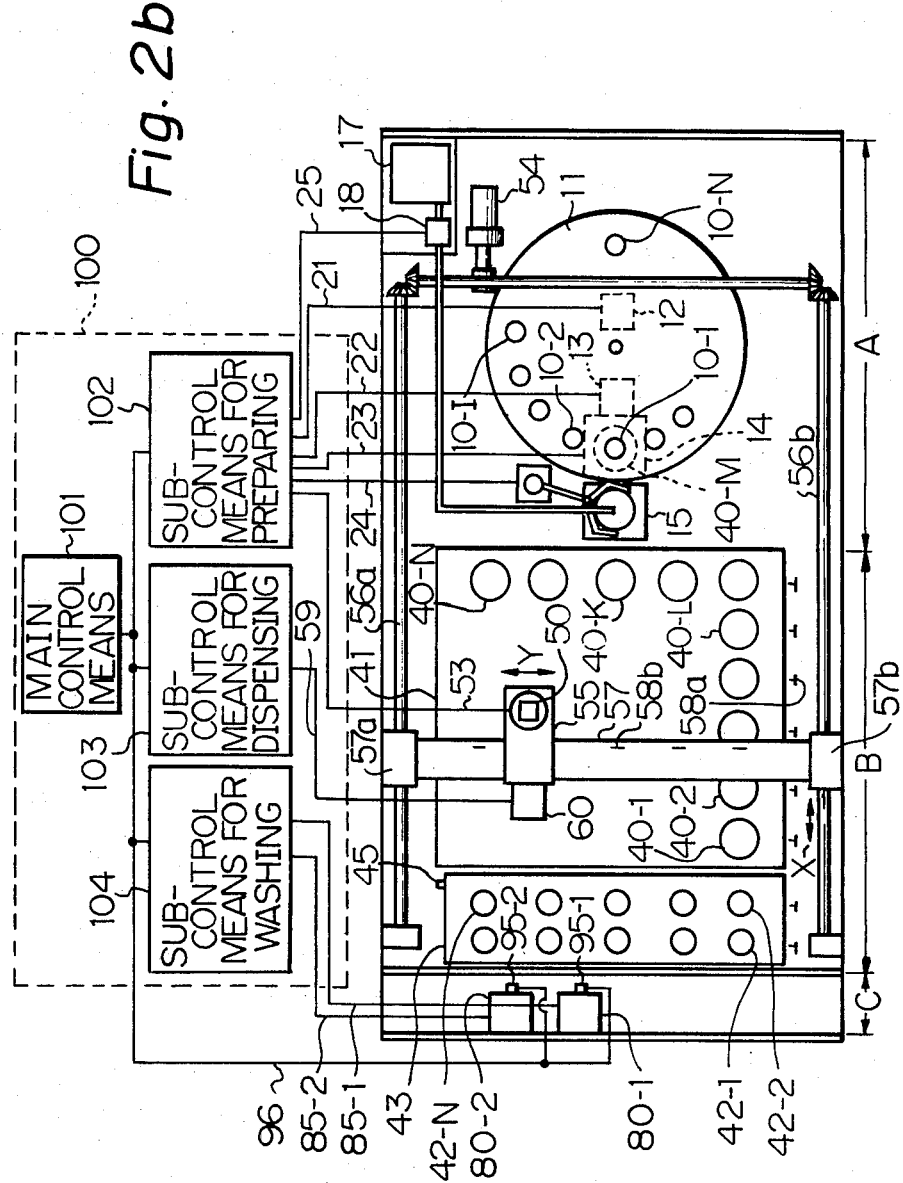
FIG. 2b is a plan view of the automatic stock preparing and dispensing system shown in FIG. 1b.

Referring again to FIGS. 1a and 2a, in this subsystem C, there are provided a plurality of pipette keeping (supplying) and washing units 80 including units 80-1, 80-2 also referred to herein as "keeping units" and "washing units", each of which keeps one or more corresponding pipetting device (hereunder sometimes referred to simply as a pipette) of a prescribed capacity 30 as to provide a supply thereof for the dispensers 60. For the purposes of simplicity, units 80-1 and 80-2 only are shown in FIG. 2b.

When a pipette of a given capacity is needed in the dispensing process, an appropriate pipetting device is selected from the the supply of pipette devices 90-1, 90-2, ... , 90-P by the control subsystem 100 and is transferred to the dispenser 60 from the corresponding pipette keeping unit in the manner which will be minutely described hereinafter. Furthermore, on exchange of the pipette or on completion of the dispensing process, the pipetting device is transferred back to the keeping unit. Sensors 95-1, 95-2 detect the transfer of pipetting devices among the dispenser 60 and the pipette keeping units 80-1, 80-2 and then send detection signals to the control subsystem 100 through a line 96.

As shown in FIG. 1a, a cistern 81 in which the pipettes are cleaned is provided beneath the pipette keeping units 80-1, 80-2, ... , 80-N and has a water renewing apparatus (not shown). Control subsystem 100 sends control signals through a line (not shown) to the water renewing apparatus so that the renewing apparatus discharges stained water at a predetermined rate therefrom and simultaneously supplies clean water at the same rate therefrom.

Figure 4:
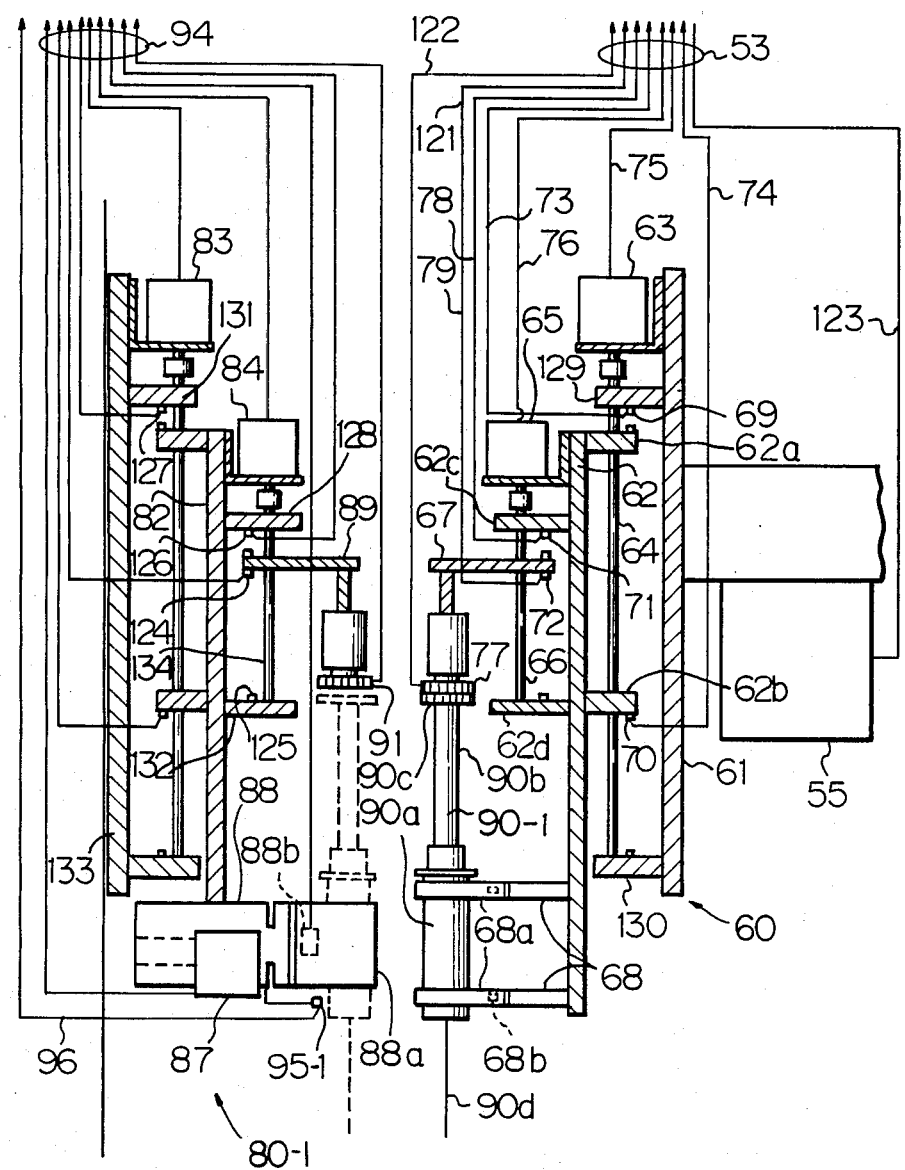
FIG. 4 is a enlarged view in elevation, partly in section, of a dispensing apparatus and a pipette keeping and washing unit of the automatic dispensing system shown in FIGS. 1a and 1b.

FIG. 4 shows the structures of the dispenser 60 which manipulate the pipette detachably attached thereto so as to take therein and discharge therefrom stock solution and of the pipette keeping and washing unit 80-1 which manipulates the 1 pipette to take therein and discharge washing solution, in detail. A stationary member 61 of the dispenser 60 is fixed to the Y-direction sliding unit 55, and a drive motor 63 for lifting up and taking down a pipetter or pipetting device such as pipette 90-1 is rigidly mounted on a fixed seat positioned at the upper end of the stationary member 61. The rotation shaft of the motor 63 is connected at one end to a vertical guide screw 64 and vertically drives a sliding part 62 which is guided along a perpendicular guide unit (not shown). A pipette holding part 68 is provided at the bottom end of the sliding part 62 and has a gripper 68a for gripping the pipetting device 90-1. The pipette keeping part 68 further has a pipette gripper operating device 68b for actuating the pipette gripper 68a so as to hold or release (detachably attach thereto) a pipetting device. The drive motor 63 drives the sliding part 62 downwardly to bring down a nozzle 90d of the device 90-1 to the prescribed depth of the stock vessel or the receptacle. Thereafter, the motor 63 is reversed and the sliding part 62 is lifted up to a height sufficient to horizontally shift the pipetting device over the stock vessels. A position sensor 69 is used to detect that the top surface of the upper protruding plate 62a of the sliding part 62 rises to the bottom surface of middle projection 129 of the stationary member 61. On the other hand, a position sensor 70 is used to detect that the bottom surface of the lower protruding plate 62b falls down to the top surface of the bottom projection 130 of the stationary member 61. These position sensors 69 and 70 may be limit switches. The detection signals from the sensors 69 and 70 are sent to the control subsystem 100 through the lines 73 and 74, respectively.

A drive unit 65, which may be a pulse motor or the like, is rigidly mounted on a seat fixed at the side of the top portion of a sliding part 62 and is connected to a vertical guide screw 66 to move a piston driving device 67 in the vertical direction. The piston driving device 67 has a coupling part 77 including an electromagnet at the bottom end thereof and the attractive force of the electromagnet connects the coupling part 77 to the top portion 90c of the pipetting device 90-1. Thus, while the piston driving device 67 rises together with the piston 90b, a cylinder 90a inhales the stock solution thereinto. In contrast, while the piston driving device 67 and the piston 90b descend together, the cylinder 90a discharges the stock solution therefrom. Sensors 71 and 72 may be limit switches or the like. The sensor 71 detects that the top surface of the piston driving device 67 comes in touch with the bottom surface of the upper projection 62c of the sliding part 62. On the other hand, the sensor 72 detects that the device 67 has reached the projection 62d of the sliding part 62. Detection signals are then sent from the sensors 71 and 72 to the control subsystem 100 through lines 78 and 79, respectively.

As is seen from FIG. 4, the structure of a pipette keeping and washing unit 80-1 is the same as that of the dispenser 60 except for the configurations of a pipette gripper 88a and a pipette holding part 88. The pipette grippers 68a and 88a are arranged to touch different parts of the cylinder 90a. Thus, the pipette grippers 68a and 88a do not interfere with each other in holding the pipetting device during a transfer as will be described below. As in case of the dispenser 60, the pipette holding part 88 has a drive device 87 and an operating device 88b of the pipette gripper 88a.

The drive device 87 may be a plunger mechanism or the like and is used to drive the pipette gripper 88a to move forward, i.e. to the right as viewed in FIG. 4 and backward, i.e. to the left as viewed in FIG. 4, between the position in which the pipetting device is held, as indicated by dashed lines in FIG. 4, and the position for transferring the pipetting device, as indicated by solid lines in FIG. 4. The operating device 88b opens the gripper 88a so as to release the pipetting device and closes the gripper 88a so as to hold the pipetting device.

The transfer of the pipetting device between the dispenser 60 and the unit 80-1 is detected by a sensor 95-1 which is located right under the pipette gripper 88a. The sensor 95-1 sends detection signals to the control subsystem 100 through a line 96.

Additionally, the pipetting device takes in clean water by raising the piston thereof and discharges stained water by lowering the piston. The body and the nozzle of the pipetting device are thus sufficiently cleaned by repeated upward and downward movement of the piston a predetermined number of times.

Control Subsystem

FIG. 5a is a schematic diagram showing the hardware configuration of the control subsystem 100.

A random access memory (RAM) 108 stores various data information as follows:

(i) the address numbers of the stock vessels on the working table 41;
(ii) the address numbers of the mixture receptacle on the rest 43;
(iii) types, colors, concentrations and current amounts of the stocks; and
(iv) other parameters for controlling the operations of the above described subsystems and so on.

Such data information are input on an input apparatus 110 which may be a keyboard or the like.

A central processor unit (CPU) 106 is used to execute various control programs and processing programs stored in a read only memory (ROM) 107 for controlling the operations of the total system and of the other subsystems above described.

A system interface unit (STO) 112 is connected with other computer systems (not shown) by means of communication lines.

Other interface units (PIO) 116, 118 and 120 are control interfaces to the dispenser 60, to the pipette keeping and washing units 80 and to external storage locations, respectively. These hardware components of the control subsystem are connected with each other by way of a common bus 105.

Operation

There are three principal processes to be performed in the above described system including:

(1) the process of dispensing stocks to prepare dyeing solvent;
(2) the process of keeping and washing pipettes; and
(3) the process of inputting various data information.

The software system of this embodiment includes four processing programs corresponding to the principal processes above and a main program for controlling the execution of such processing programs. Further, an operating system applicable to a multitasking system as known to those skilled in the art is adopted in this dispensing system so that the above described principal processes can be performed substantially in parallel with each other.

Moreover, it is desirable that the real-time operating system as known in the art is adopted in this automatic system whereby the current statuses of the processes are displayed on a monitor and an operator can interrupt the execution of the processing programs at any appropriate moment.

Hereinafter, referring to flow charts of the above stated processing programs shown in FIGS. 6a, 7a, 9, 10, the operation of the automatic system will be described in detail.

An Overall Outline of the Processes in the System

Figure 6A:
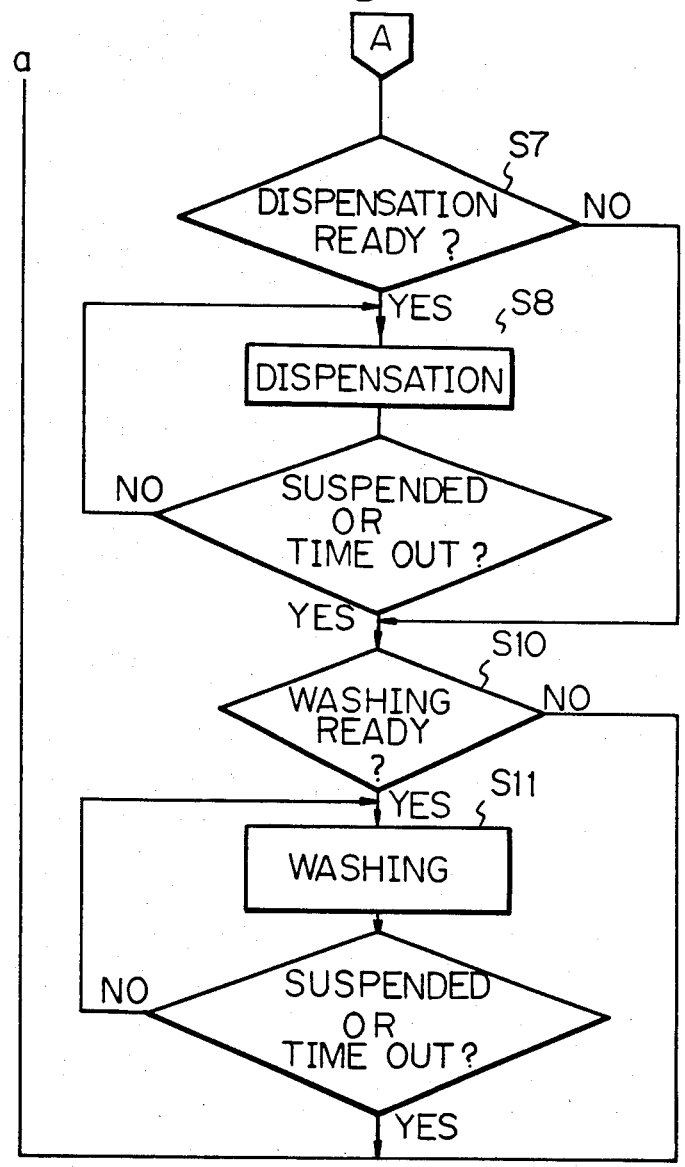

Referring now to FIG. 6a showing a flow chart of an example of the main program, the processes of inputting the data information (step S2), dispensing stock (step S8) and washing pipettes (step S11) are substantially performed in parallel with each other.

In addition, the adoption of a multitasking system makes possible the following operations. For instance, when a pipette provided in the dispenser is exchanged for another one, the process of dispensing stock solutions to receptacles with the new pipette and the process of washing the used pipette are also performed simultaneously.

In such an operating system, when an interruption to a task for the processing programs under execution is generated, the interrupted task is placed in the wait state and another task having been in the ready state is now executed. For example, when an event such as rotation of the rotary table 11 occurs during the execution of the program for preparing a sample, the operating system generates an interruption to the task of preparing stock solutions and processing is put on hold.

Input Processing

Figure 7A:
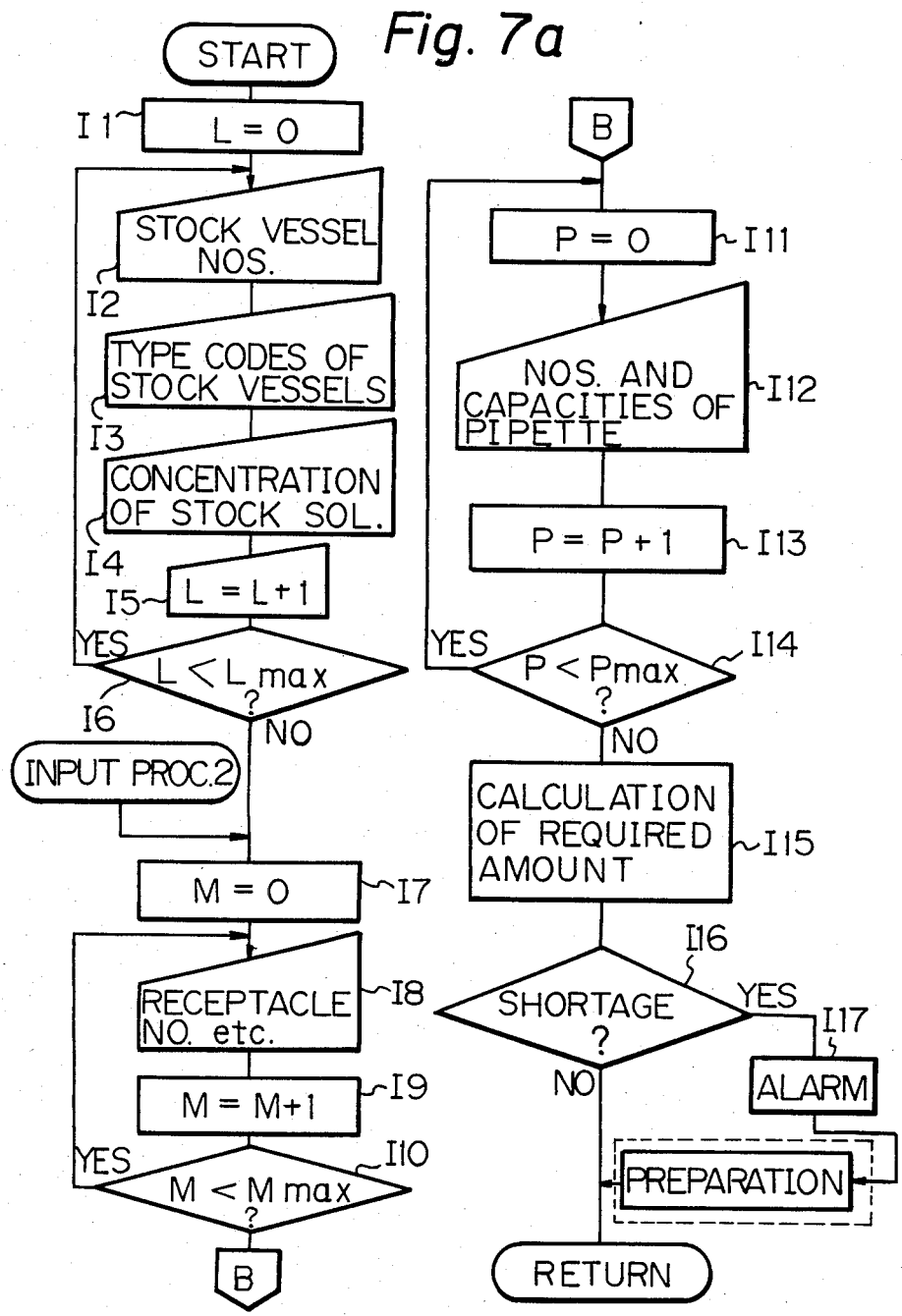

FIG. 7a is a flow chart of an example of input processing programs. First, input processing shown in FIG. 7a will be explained hereinbelow.

First, in step I2, an operator inputs data information on stock solution to be supplied to each stock vessel in the order of stock vessel number or address on the table 41 from the input apparatus 110. Further, in step I3, the operator also inputs the data information concerning mixtures of stock solutions to be prepared in each receptacle in the order of the receptacle number and inputs the data information concerning each of the pipetting devices in the order of pipetting device number. These input data are then loaded on the RAM 108. In step I8, types and amounts of the stock solutions to be mixed in each receptacle is further input. $M_{max}$ in step I10 indicates the maximum number of receptacles which can be accommodated by the rest 43.

Thereafter, the capacity of the pipette and the number of times of repeating the raising and lowering of the piston is input for each pipette in the step I12. $P_{max}$ in the step I14 indicates the maximum number of pipettes to be kept in all the pipette holding units.

After the input information on the stock solution, solvent mixture and the pipettes above described is loaded on the RAM 108, the required quantity of each type of stock solutions for the dispensing process is calculated in the control subsystem in the step I15 and is compared with the previously input amounts of the stock solutions currently reserved in the corresponding vessels in the step I16. If the quantity of any types of solutions is insufficient, the program enters step I17 and an alarm is then issued.

If all the stock solutions are sufficient in amount for dispensing; the main program proceeds to the dispensing process.

Dispensing Process

Figure 9B:
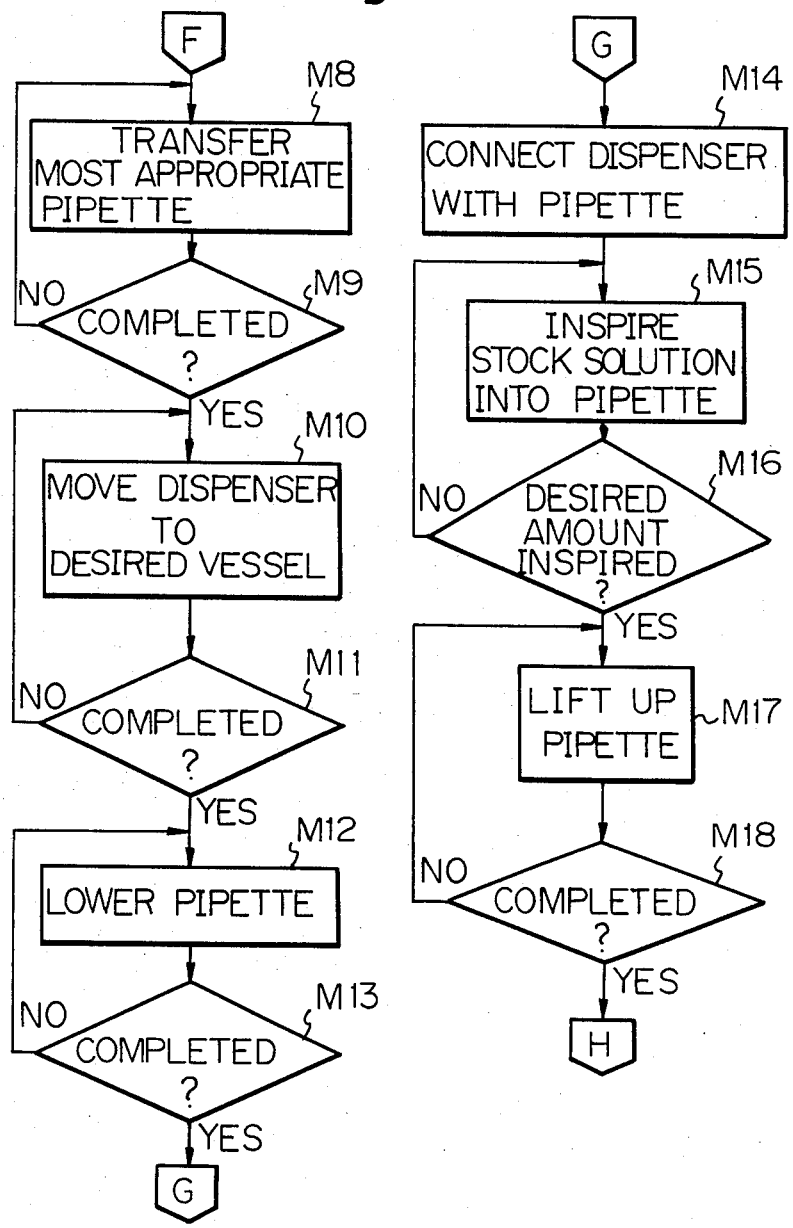
Figure 9C:
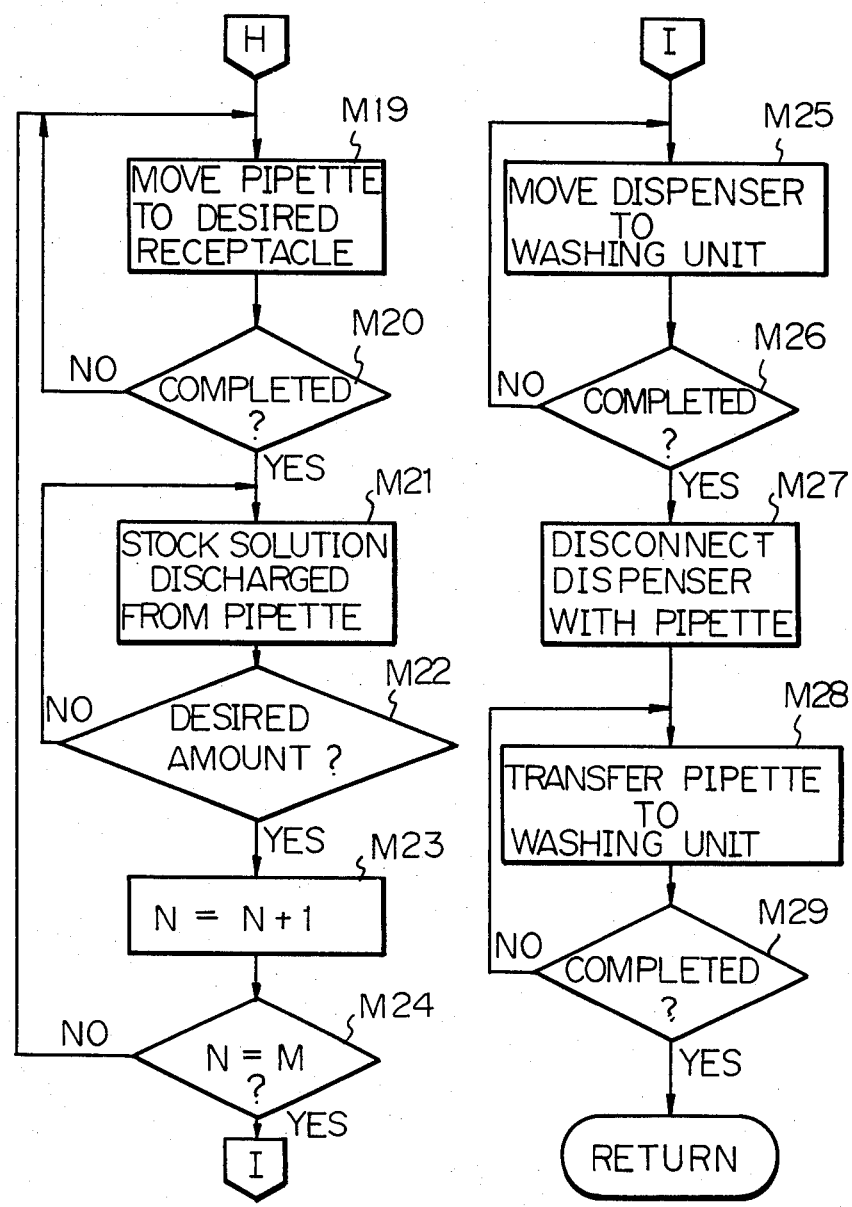

FIG. 9 is a flow chart of an example of the dispensing process program. First, based on information such as types and required amounts of the stock solution to be mixed, viscosities of the stocks and capacities of all the pipettes which are input in the step I12 of the input processing program, the most appropriate pipette for the dispensing process which will be effected thereafter is determined (step M1). Thereafter, inspection is made as to whether or not the selected pipette is sufficiently washed (step M2). As will be described below, a used pipette is kept in the keeping unit corresponding to the address number of the pipette and is washed while the other pipettes are used for dispensing. Furthermore, the pipette keeping and washing subsystem has an adequate number of kinds of pipettes according to their respective frequency of use. Therefore, on inspection, the selected pipette will normally have already been cleaned up.

If sufficiently clean, it is next examined by means of the sensor 45 to check whether or not the rest 43 is properly placed at the predetermined initial position (step M3). If not sufficiently clean, the program inspects again after a predetermined interval of time because the selected pipetting device is being washed.

If appropriately positioned, the drive unit 54 and the sliding unit 55 are activated to move the dispenser 60 to the predetermined initial position which may be the upwardly leftmost corner of the table 41 shown in FIG. 2. When the dispenser 60 stops, whether or not the dispenser 60 rests at the proper position is verified by comparing the current position of the dispenser 60 detected by the sensors 58a and 58b with the predetermined initial position for each washing unit 80, data on which are stored in the RAM 108.

In the event that the receptacle rest 43 is not properly positioned or that the dispenser does not stop at the predetermined position, the program proceeds to step M5 and then an alarm is issued. The operator investigates the causes and removes the obstacles by the following steps:

(1) moving the rest 43 to the proper position; and/or
(2) transferring the dispenser 60 to the predetermined initial position.

The system has then become ready to start the dispensing process. The program next advances to step M6 and the dispenser 60 moves to the position in front of the washing unit 80, here which assumed to be unit 80-1 which keeps the most appropriate pipette (step M6). After the sensors 58a and 58b detect that the dispenser 60 has reached the predetermined position in step M6, the most appropriate pipette is transferred from the keeping unit to the dispenser 60 (step M7) in the following manner. Here, it is now assumed that the pipette 90-1 is selected to be the most appropriate one. First, the gripper drive unit 87 is activated and forces the gripper 88a to the position where the pipette is fitted into the gripper 68a of the dispenser 60. The sensor 95-1 detects the transfer of the pipette 90-1 from the unit 80-1 to the dispenser 60 and sends detection signals to the CPU 106 through the interface 118. Thereafter, the gripper operating unit 88b operates and the gripper 88a releases the pipette 90-1. Then, the drive unit 87 is reversed to put back the portion 88a to the initial position shown in the solid lines in FIG. 4 (steps M8 and M9).

After the transfer of the pipette from the unit 80-1 to the dispenser 60 has been completed in this way, the dispenser 60 moves to a position right above the desired stock vessel in the same manner as above described with reference to the steps M6 and M7. Thereafter, the motor 63 is activated and rotates the screw 64 so that the sliding part 62 glides down the lower projection 130 of the stationary member 61 (step M13). When the sensor 70 detects that the sliding part 62 has reached the projection 130, the detection signal is sent to the control subsystem 100 therefrom through the line 74. The control subsystem 100 activates the piston drive unit 65 in responsive to the signal and lowers the piston driving device 67 until the electromagnet in the coupling part 77 comes in contact with the top end portion 90c of the piston (step M14).

Thereafter, in order to inspire the stock solution into the cylinder 90a, the piston driving device 67 and the piston 90b rises by an amount corresponding to the required amount of the stock solution (steps M15 and M16). It is desirable for effectively dispensing a certain kind of stock solution into a plurality of receptacles that the sum of the required amounts of the stock solution for each receptacle is first taken into the cylinder at one time.

When the required amount of the stock solution is taken into the cylinder 90a, the drive motor 63 is reversed. Then, the sliding part 62 rises together with the pipetting device until the sensor 69 detects that the top surface of the part 62 is touching the bottom surface of the upper projection 129 of the stationary member 61.

Thereafter, the dispenser 60 moves to the desired receptacle in the same way as the steps M16, M17 and M18 above described (step M19).

On successful completion of the transfer of the dispenser 60, the program enters step M20, whereupon the pulse motor of the drive unit 65 rotates the screw 66 in the opposite direction and the piston driving device 67 slidingly goes down by an amount corresponding to the amount of stock solution to be discharged from the cylinder 90a. If a certain kind of stock solution is to be distributed to a plurality of receptacles, the loop composed of steps M18 to M24 is repeatedly executed M times. Here, M denotes the number of receptacles to be dispensed with the stock solutions. Thereafter, the dispenser 60 returns to the above described position in front of the pipette keeping unit 80-1 (step M25) and it is then verified by use of the sensors 58a and 58b whether or not the dispenser 60 have reached the proper position (step M26). When the dispenser 60 is affirmed to be at the predetermined position, the control subsystem 100 issues control signals to demagnetize the electromagnet of the coupling part 77 so as to disconnect the part 77 from the top end portion 90c of the piston 90b. Thereafter, the piston driving portion 67 rises and immediately after the sensor 71 detects that the top surface of the portion 67 has reached the bottom surface of the middle projection of the sliding part 62, the drive device 87 and the operating device 88 are activated and the gripper 88a is forced to the right in FIG. 4 to catch the cylinder 90a of the pipetting device.

Thereafter, the gripper 88a returns to its initial position. In this way, the pipetting device 90-1 is transferred to the unit 80-1 (step M28). When the sensor 95-1 detects the received pipetting device 90-1, detection signals are sent to the control subsystem 100 through the line 96 (step M29).

Thus, the process of dispensing one kind of stock solution to the receptacles is completed. With respect to other different kinds of stock solutions, the program returns to the step M1 and repeats the operation from the step M2 to the step M29. The used pipetting device 90-1 is to be washed out in the washing processing which will be described hereinbelow.

Processing of washing the Pipetting Devices

Figure 10A:
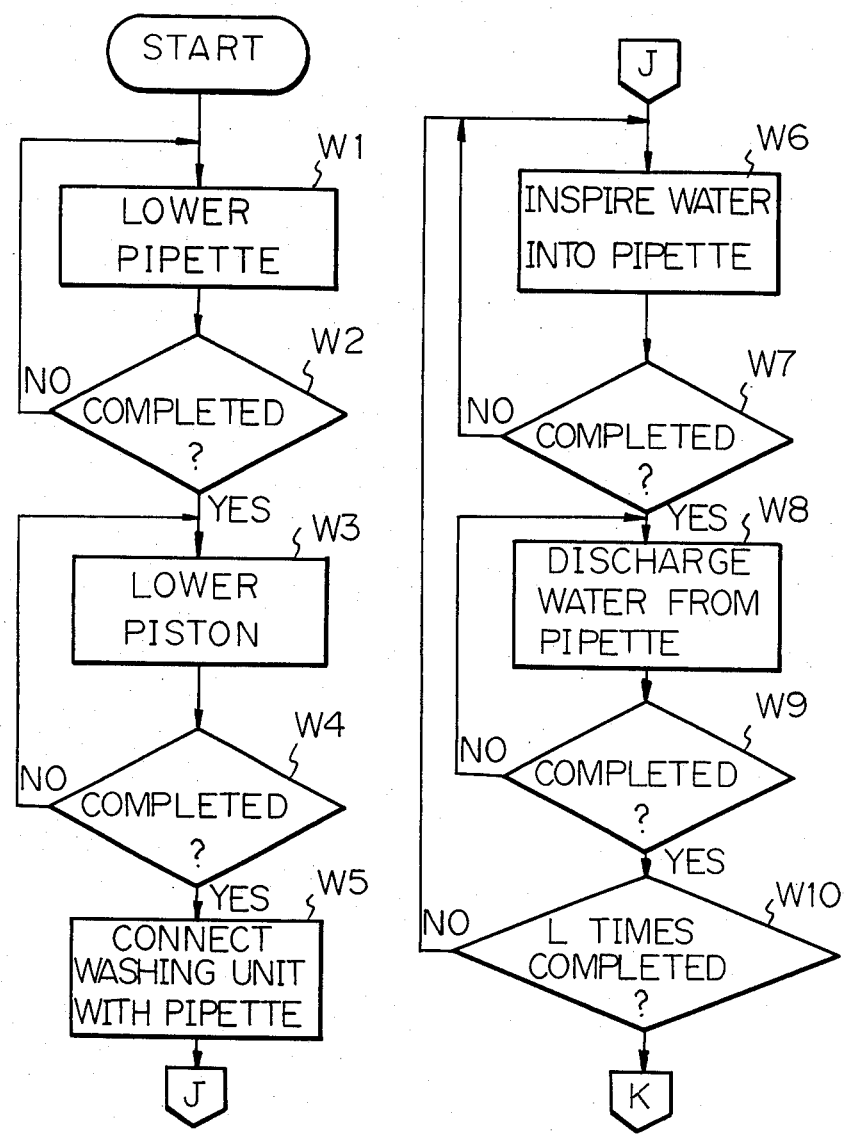
FIGS. 10a and 10b provide a flow chart of a subprogram for controlling the pipette washing process.
Figure 10B:
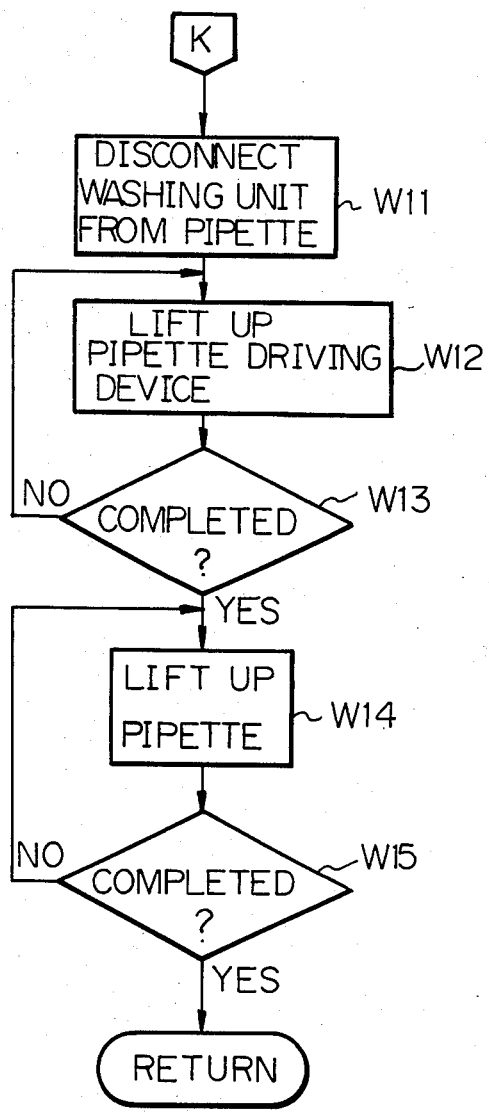

FIG. 10 is a flow chart of an example of a processing program for washing the pipetting devices.

In step W1, the program activates the motor 83 and causes the sliding part 82 to glide down by the predetermined distance so that the nozzle 90d of the pipetting device 90-1 dips into the cistern 81 (step W2).

Thereafter, the program enters step W3, whereupon the piston drive unit 84 is activated and rotates the screw 134 so as to lower the piston drive portion 89. The piston drive portion 89 continues to descend further until the sensor 124 detects that the top arm of the portion 89 has come in touch with the bottom projection of the sliding part 82 (steps W3 and W4). During this, the piston 90b continues to be forced down to discharge the stock solution left in the cylinder 90a into the cistern 81.

Thereafter, the program proceeds to step W5, whereupon the electromagnet of the coupling part 91 is magnetized and the top end portion 90c of the piston 90b is rigidly connected to the part 91 by the attractive force of the electromagnet.

The program next proceeds to the loop consisting of steps W6 and W7, whereupon the pulse motor of the drive unit 84 is reversed and the piston drive portion 89 ascends together with the piston 90b until the sensor 126 detects that the portion 89 has reached the middle projection 128 of the sliding part 82. Thus, the pipetting device takes up water into the cylinder 90a thereof.

Thereafter, the program enters the loop consisting of steps W8 and W9, whereupon the piston drive unit 84 again forces the piston 90b to go down and to push down the cylinder 90a in order to discharge water out thereof.

In this way, the piston 90b alternately ascends and descends L times (step W10). L is suitably predetermined in such a manner that the cylinder 90a and the nozzle 90d can be sufficiently cleaned and is previously input in the step I12 of the input processing (FIG. 7a). Upon completion of washing the pipetting device, the electromagnet of the portion 91 is demagnetized. This causes the portion 91 to separate from the piston 90b. Thereafter, the piston driving device 89 rises up to the middle projection 128 (steps W11, W12 and W13), and the sliding part 82 moves up until the sensor 127 detects that the part 82 has reached the middle protruding plate of the stationary member (steps W14 and W15). The process of washing a pipetting unit is thus completed.

Additionally, in a case where material adhered to the inner wall of the cylinder substantially deteriorates the accuracy of dispensing the stocks, such a problem can be solved by provision of means for desiccating the adhered material in the pipette keeping units. For instance, a small fan forced heater may be equipped within each pipette keeping unit for blowing hot air onto the stock solution before washing the pipetting device.

Hereinafter, another preferred embodiment will be described in detail.

FIGS. 1b and 2b respectively show the overall front and plan views of an automatic dispensing system adopted subsystem for preparing stock solutions embodying the present invention. In these drawings, reference character A designates a stock preparing subsystem in which desired stock solution such as a dyeing mother solution is prepared by diluting dye or dyeing auxiliary with diluent such as water or the like.

Reference character B indicates a dispensing subsystem and reference character C designates a pipette keeping and washing subsystem.

Figure 5B:
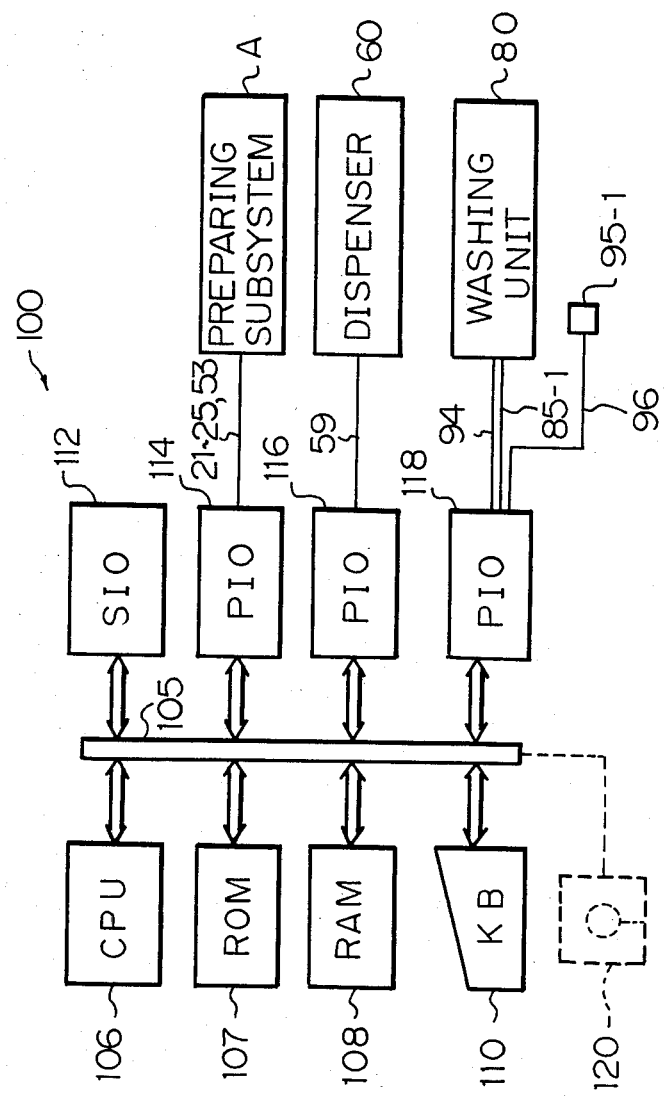
FIG. 5b is a block schematic diagram showing a control subsystem of the automatic stock preparing and dispensing system show in FIG. 1b.

Reference numeral 100 indicates a control subsystem including a computer for controlling the operations of the subsystems above. In these drawings, the functional structure of the control subsystem of this embodiment is shown as in FIGS. 2a and 2b. The hardware configuration of the control subsystem is shown in FIG. 5b and will be described below.

This embodiment is different from the previously described embodiment in the respects that the system is further provided with a stock solution preparing subsystem and that the dispensing subsystem and the control subsystem need additional components communicating with the stock solution preparing subsystem.

Stock Preparing Subsystem

Referring to FIGS. 1b and 2b, respective raw material containers 10-1 to 10-N are detachably fixed at the peripheral portion of a rotary table 11 around the circumference thereof.

The rotary table 11 is rotatably fitted to a vertical shaft 19 and is rotated by a drive motor 12 which is connected to the subcontrolling means 102 by way of a line 21.

A raw material dropping apparatus 13 is used to feed a raw material such as dye or dyeing auxiliary out of the raw material container 10-1 down into a stock vessel 40-M. The raw material dropping apparatus 13 is connected to the subcontrolling means 102 through a line 22 and thus the operation of dropping the raw material into the stock vessel 40-M is controlled by commands from the computer of the control system 100, in which the quantity of the raw material to be fed is predetermined for each raw material container. A stock measuring apparatus 14 such as a load-cell-scale is used to measure the quantity of raw material dropped into the stock vessel 40-M. Upon completion of the measurement, the stock measuring apparatus 14 generates signals indicating the measured value of the raw material and sends the signals to the subcontrolling means 102 through a line 23.

The stock vessel 40-M is transferred from the dispensing subsystem B and is put on a temporary stock vessel stand 15 as shown by dotted lines in FIG. 1b until a stock vessel transporting apparatus 16 moves the stock vessel 40-M to the position shown by solid lines in FIG. 1b on the measuring apparatus 14 for feeding the raw material into the vessel 40-M. After the quantity of the dropped raw material is thus measured, the vessel 40-M is moved back onto the stand 15 by the vessel transporting apparatus 16. Such operation of the transporting apparatus 16 is controlled by signals sent out from the subcontrolling means 102 through a line 24.

A diluent feed apparatus 18 supplies a desired amount of diluent such as water from a diluent tank 17 to the stock vessel 40-M on the stand 15 through a conduit 20 under the control of the subcontrolling means 102 which issues control signals to the apparatus 18 through a line 25.

Figure 3:
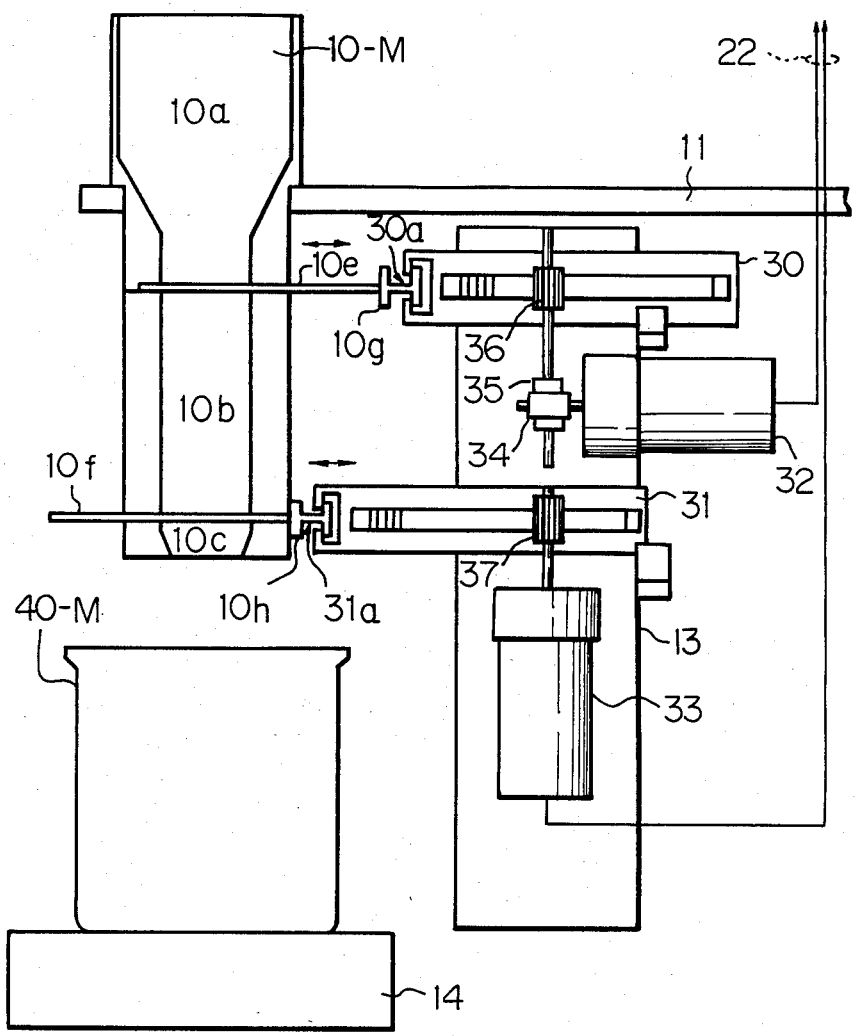
FIG. 3 is an enlarged view in elevation, partly in section, of a stock preparing subsystem of the automatic preparing and dispensing system shown in FIG. 1b.

FIG. 3 illustrates the construction of the raw material dropping apparatus 13 and that of the stock vessel 40-M in detail. The vessel 10-M includes a stock reserving chamber 10a, a stock determination chamber 10b and an outlet port 10c. A top shutter 10e is provided as a boundary between the chambers 10a and 10b, and a bottom shutter 10f is also provided as a boundary between the chamber 10b and the port 10c.

The raw material dropping apparatus 13 includes a top shutter operating unit 30 and a bottom shutter operating unit 31. The top shutter operating unit 30 is connected to the top shutter 10e and is driven by a drive motor 32 by way of a set of gears 34, 35 and 36. When the operating unit 30 is forced to move leftwards, as viewed in FIG. 3, the top shutter 10e cooperates with the operating unit 30 and also moves leftwards to close the boundary between the chambers 10a and 10b. In contrast with this, when the drive motor 32 rotates the shaft of rotation thereof in the opposite direction, the top shutter operating unit 30 is in turn moved rightwards, as viewed in FIG. 3, and pulls the top shutter 10e in the same direction so as to open up the boundary between the chambers 10a and 10b, thereby supplying the stock of the reserving chamber 10a to the determination chamber 10b.

On the other hand, the bottom shutter operating unit 31 is connected to the bottom shutter 10f and driven by the motor 33 through a gear 37. When the bottom shutter operating unit 31 is forced to move leftwards, as viewed in FIG. 3, the bottom shutter 10f cooperates with the operating unit 31 and is pushed in the same direction so as to shut the boundary between the chamber 10b and the outlet port 10c. When the drive motor 33 rotates the shaft of rotation thereof in the reverse direction, the operation unit 31 pulls the bottom shutter 105 rightwards, as viewed in a FIG. 3, and opens the boundary between the chamber 10b and the port 10c. This results in the raw material in the chamber 10b falling into the stock vessel 40-M through the outlet port 10c. Such operation of the motor 33 is controlled by commands from the subcontrolling means 102 such as to be related to the operation of the motor 32.

In FIG. 3, the shutter 10e is shown at the position for opening the boundary between the chambers 10a and 10b, while on the other hand the shutter 10f is shown at the position for closing the chamber 10b and the outlet port 10c.

Incidentally, it should be understood that the raw material dropping apparatus can be modified according to the type and inherent properties of the raw materials to be used for making stock solutions.

Dispensing Subsystem

Referring back to FIGS. 1b and 2b, the dispensing subsystem of this embodiment has the same structure as that of the embodiment already shown in FIGS. 1a and 2a, except for a robot hand unit 50.

The robot hand unit 50 is used to transfer one of the stock vessels between the stock preparing subsystem and the dispensing subsystem. An arm 51 of the robot hand unit 50 is operative to vertically expand or contract and has a grasping mechanism portion 52 at the bottom end thereof to catch hold of the stock vessel.

The robot hand unit 50 and dispenser 60 are fixedly attached to a sliding unit 55 which is operative to slide on a sliding rail 57c in Y-direction, denoted by arrow heads a FIG. 2b, and is moved in the X-direction shown in FIG. 2b by the driving force of a drive unit 54 by way of the guide shafts 56a and 56b.

The robot hand unit 50 is thus capable of transferring any stock vessel between the stock preparing subsystem A and the dispensing system B. Similarly, the dispenser 60 can carry any pipette between the dispensing subsystem B and the pipette keeping units in the subsystem C. Further, the current positions of the robot hand unit 50 and of the dispenser 60 are detected by sensors 58a for detecting objects existing in the Z-direction and sensors 58b for detecting objects existing in the Y-direction, from which sensors appropriate detection signals are sent to the control subsystem 100 through a line (not shown).

Pipette Keeping and Washing Subsystem

As is seen from FIGS. 1b and 2b, the pipette keeping and washing subsystem of this embodiment has the same structure as the corresponding subsystem of the previously described embodiment shown in FIGS. 1a and 2a.

Control Subsystem

FIG. 5b is a schematic diagram showing the hardware configuration of the control subsystem 100 of this embodiment.

In comparison with the control subsystem of the previously described embodiment shown in FIG. 5a, the differences are as follows:

(i) A random access memory (RAM) 108 of this embodiment stores additional data information such as the address numbers of the stock containers on the rotary table 11 and so on.

(ii) The control subsystem of this embodiment is provided with another control interface unit (PIO) 114 relative to the units of the stock preparing subsystem A.

Operation

There are four principal processes to be performed in the above described system of this embodiment, as follows:

(1) the process of preparing stock solution and storing the stock solution in stock vessels;
(2) the process of dispensing stock solution to prepare dyeing solvent;
(3) the process of keeping and washing pipettes; and
(4) the process of inputting various data information.

However, the procedure of dispensing stock solution and that of keeping and washing pipettes in this embodiment are the same as in the previously described embodiment. Therefore, referring to flow charts of the above stated processing programs, the flow charts of which are shown in FIGS. 6b, 7a, 7b and 8, the operation of this embodiment will be described in detail hereinbelow with regard only to an outline of the entire processes, the input process and the process of preparing stock solutions and storing the stock solutions in stock vessels.

An Overall Outline of the Processes in the System

Referring now to FIG. 6b showing a flow chart of an example of the main program, the processes of inputting the data information (step S2), preparing stock (step S5), dispensing stock (step S8) and washing pipettes (step S11) are performed substantially in parallel with each other.

In addition, the adoption of a multitasking system also makes possible the following operations. For instance, after a stock vessel is transferred to the stock preparing subsystem A, the process of preparing stock solution in the moved vessel and the process of dispensing stock solutions of the other vessels are simultaneously effected substantially in parallel with each other.

Input Processing

Figure 7B:
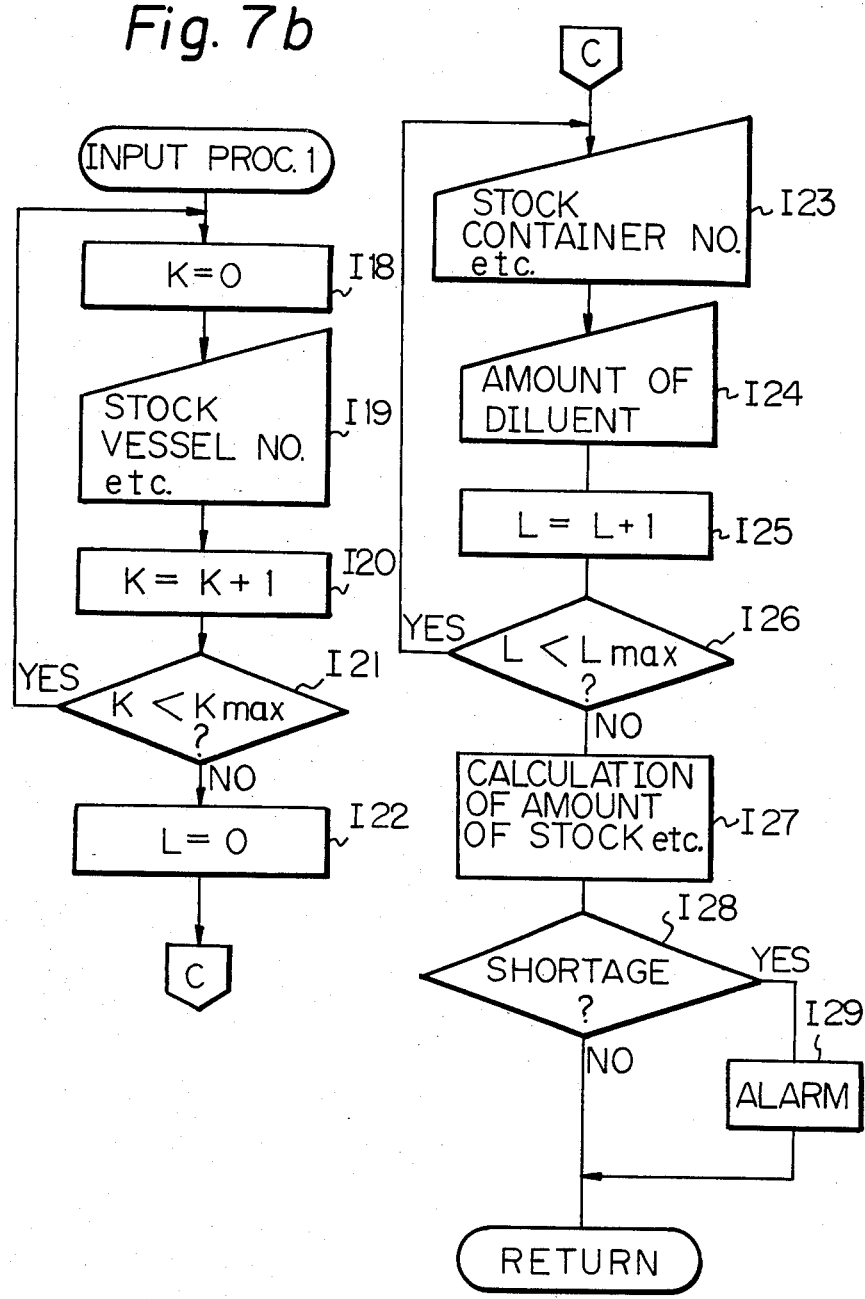
FIG. 7b is a flow chart of a subprogram for inputting data information into the automatic stock solution preparing and dispensing system shown in FIG. 1b.

FIGS. 7a and 7b are flow charts of examples of input processing programs. First, input process 1 shown in FIG. 7b will be explained hereinbelow.

In steps I18 to I22, an operator inputs the following data information for each stock vessel having an address number from an input device such as a keyboard or the like:

(a) types, required amounts and concentrations of the stock solutions to be put or prepared in the stock vessels;

(b) the first prescribed quantity of the raw material for dilution thereof and the second prescribed quantity of the raw material for fine adjustment of the amount thereof in the stock vessel, which will be referred to below in the description of the "Stock Preparing Process"; and so on.

Incidentally, the operation of the system will be described herein on the assumption that control parameters such as $K_{max}$ have been already input at the initial setting of the system. In the step I22, $K_{max}$ denotes the maximum number of stock vessels to be put on the table 41.

Thereafter, in the steps I23 to I26, the types and required quantities of the raw materials to be put in the stock containers and the required amount of water for diluting the raw materials in the containers and so on for each of the raw materials containers are input from the input device. $L_{max}$ shown in the step I26 designates the maximum number of stock containers being held on the rotary table 11.

The above input information is loaded on the RAM 108. Thereafter, the required amounts of the raw materials and diluent are roughly estimated for each stock vessel in the step I27. The estimated values of the required raw materials and diluent are then compared with the amounts of the raw material currently kept in the corresponding containers and diluent currently reserved in the diluent tank 17 in the step I28. If any shortage of the raw materials or diluent becomes clear from the result of comparison, an alarm is issued and the operator supplies the amount of short-fall in the raw material or diluent in the step I29. If the amounts of the raw material or diluent are sufficient, the program proceeds to the step 17 of input processing 2 shown in FIG. 7a.

After the input information on the dyeing solution and on the pipettes above described is loaded on the RAM 108, the required quantity of each type of stock solution for the dispensing process is calculated in the control subsystem in the step I15 and is compared with the previously input amounts of the stock solutions currently reserved in the corresponding vessels in the step I16. Any shortage of the stock solution is to be supplemented in the stock preparing and storing process.

If the stock preparing process is known to be unnecessary, input process 1 can be omitted and input process 2 may be performed above. In this case, the entry point of the input processing program from the main program is set at the beginning of the input process 2 by a known technique such as use of a control parameter.

Stock Preparing Process

Figure 8B:
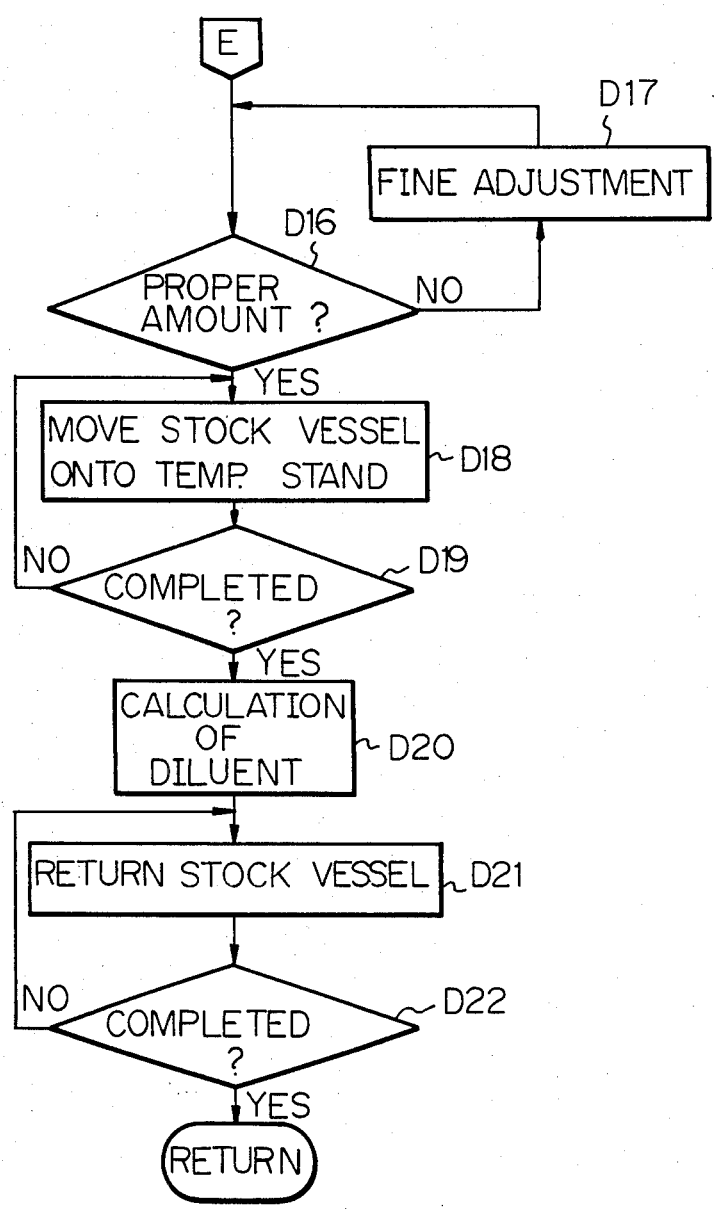

FIGS. 8A and 8B show is a flow chart of an example of the program for the stock preparing and storing process. In step D1, the drive unit 54 and the sliding unit 55 cooperate in transferring the robot hand unit 50 to a position right above the desired stock vessel 40-M. During the transfer of the unit 50, the drive unit 54 and the sliding unit 55 are controlled by the subcontrolling means 102 on the basis of the address information of the vessels previously given in the input processing and the current position information of the robot hand unit 50 from the sensors 58a and 58b. After the completion of this transfer is detected by the sensors 58a and 58b in the step D2, the arm 51 stretches downwardly by a prescribed distance and the gripping portion 52 catches the vessel 40-M in the step D3. Thereafter, the arm portion 51 goes up to lift the vessel to the previously input height at which the vessel 40-M can be horizontally shifted without interference with the other vessels and so forth. Further, after the drive unit 54 and the sliding unit 55 move back the robot hand unit 50 with the vessel 40-M to the position right above the stock vessel stand 15, the arm 51 again stretches and takes down the stock vessel 40-M in the step D4. When the arm portion 51 stretches by the preadjusted distance and thus the vessel 40-M reaches the upper surface of the stand 15 (step D5), the gripping portion 51 releases the vessel 40-M and subsequently the robot hand unit 50 rises and returns to the predetermined initial position.

The program next advances to step D6, whereupon the vessel transporting apparatus 16 is activated and catches the vessel 40-M by closing a hand thereover and transports the vessel to the preadjusted position on the stock measuring apparatus 14. Immediately after the transporting apparatus 16 releases the vessel, zero point adjustment of the measuring apparatus 14 is effected (step D8). Next, the rotary table 11 rotates to set the required stock container 10-M at the position shown in FIG. 3 for dropping the raw material into the stock vessel 40-M (steps D9 and D10). Thereafter, the top shutter 10e is coupled to the top shutter operating unit 30 by horizontally shifting a projection of the shutter 10e having H-shaped section 10g into a groove 30a of the operating unit 30. In a similar way, a projection of the bottom shutter 10f having H-shaped section 10h is horizontally shifted into a groove 31a of the operating unit 31 and thus the bottom shutter 10f is coupled to the operating unit 31. At that time, the top shutter 10e still closes up the boundary between the chambers 10a and 10b and the bottom shutter 10f also closes the outlet port 10c. The raw material determination chamber is normally filled with the raw material.

The program next enters step D11 via branch "YES", whereupon the bottom shutter operating unit 31 is activated and moves to the right, as viewed in FIG. 3, together with the shutter 10f so that the raw material in the chamber 10b falls down into the vessel 40-M through the outlet port 10c. In order to more completely drop the raw material from the chamber 10b, it is desirable that either the bottom shutter 10f alone repeatedly opens and closes or a vibrator (not shown) is connected to the stock container 10-M to suitably vibrate the bottom shutter 10f.

In practice it is, however, very difficult to drop the precise amount of the required raw material, especially of the powdery dye in spite of the provision of such a vibrator. For example, even if the raw material determination chamber 10b has a capacity accurately equal to the volume of dye of 5 grams, the amount of the actually dropped dye is usually 4.6 grams or thereabouts.

To eliminate this drawback of the prior art, the amount of the raw material actually dropped into the stock vessel is measured by the measuring apparatus 14 (step D12).

In step D13, the bottom shutter operating unit 31 and the shutter 10f return to the left, as viewed in FIG. 3, so as to close the boundary between the chamber 10b and the outlet port 10c.

At the time the program advances to step D14, the control subsystem activates the top shutter operating unit 30 to pull up the top shutter 10e to the right, as viewed in FIG. 3. The boundary between the chambers 10a and 10b is thus opened and the raw material goes down from the chamber 10a into the chamber 10b. As in the case of the step D11, the swaying motion of the top shutter 10e caused by either the operating unit 30 or a vibrator (not shown) is preferable so as to more thoroughly drop the raw material into the chamber 10a.

The program further advances to step D15, whereupon the top shutter operating unit 30 is forced back to the left, as viewed in FIG. 3, so as to close the top shutter 10e.

Thereafter, the measured amount of the raw material actually fed into the vessel is compared with the prescribed first amount of the raw material, e.g. 4.5 grams, which is previously input during the step I2 of the flow chart of the input processing program shown in FIG. 7. If the measured amount is less than the initially prescribed one, the program proceeds to branching step D17 and the bottom shutter 10f is again opened to drop the raw material in the chamber 10b by the second prescribed amount, which is also previously input during the step I2. Here it should be noted that raw material of a greater quantity than the capacity of the chamber 10b can be dropped if the first prescribed amount (parameter) is appropriately selected to be greater than the capacity of the chamber 10b.

On the other hand, if the previously measured amount of the raw material is more than or equal to the first prescribed amount, the program goes forward to step D18, whereupon the transporting apparatus 16 once again catches the stock vessel 40-M and transports it to the stand 15. On completion of the transportation of the vessel (step D19), the amount of diluent to be supplied to the raw material in the stock vessel is calculated in CPU 106 by using data such as the amount of the raw material measured at the step D11 and the required concentration of the stock solution. Thereafter, signals indicating the result of calculation are sent to the diluent feed apparatus 18. This apparatus 18 supplies the required amount of water into the stock vessel 40-M from the diluent tank 17 through the conduit 20 (step D20) in response to these signals. When the injection of diluent is finished, the robot hand apparatus 50 is transferred to the position right above the stand 15 by operating the drive unit 54 and the sliding unit 55. In reverse, as at the steps D3 and D4, the robot hand apparatus 50 carries the vessel 40-M to the predetermined position on the working table 41 (step D21).

In addition, it is possible to further dilute the stock solution thus prepared in the following manner. First, the required amount of the requisite type of stock solution is extracted from the stock vessel and injected into an appropriate empty vessel 40-K by means of the dispenser 60. Thereafter, the vessel 40-K is transferred by the robot hand unit 50 onto the stand 15 in the same way as in case of the stock vessel 40-M. After the required amount of diluent is poured into the vessel 40-K by way of the diluent feed apparatus 18, the robot hand unit 50 carries back the vessel 40-K to the initial predetermined position on the table 41.

While the invention particularly shown is described with reference to a preferred embodiment thereof, it will be apparent to those skilled in the art that various modifications and variations could be made to the embodiment of the invention as hereinabove described without departing from the spirit and scope of the invention.

We claim:

1. An automatic dispensing system, comprising:
   means for supplying a plurality of pipettes, each being manipulatable for taking stock solutions therein from stock vessels and discharging the stock solutions therefrom into receptacles;
   means, detachably attachable to a selected pipette of the plurality of pipettes, for manipulating the selected pipette when detachably attached thereto so as to take in the stock solution from the stock vessels and so as to discharge the stock solution therein to the receptacles;
   said supplying means including means, detachably attachable to the selected pipette, for washing the selected pipette of remaining stock solution therein when detachably attached thereto after being manipulated by said manipulating means;
   pipette transferring means for transferring the selected pipette for said supplying means to said manipulating means so as to be detachably attached thereto, and for transferring the selected pipette from said manipulating means to said washing means so as to be detachably attached thereto; and
   control means for controlling said manipulating means, said washing means, and said pipette transferring means, said control means including:
   means for automatically selecting a first pipette and a second pipette of the plurality of pipettes to be provided to said manipulating means, and
   means for controlling said pipette transferring means, said manipulating means and said washing means such that the first pipette and the second pipette are in turn automatically successively transferred to said manipulating means, detachably connected to and manipulated by said manipulating means so as to take in the stock solution from the stock vessels and so as to discharge the stock solution therein to the receptacles, transferred to said washing means and washed by said washing means, and such that the first pipette is washed by said washing means while the second pipette is being manipulated by said manipulating means.

2. The system set forth in claim 1 wherein said control means controls said pipette transferring means, said manipulating means and said washing means in a time-division multiplex mode so that the taking in and discharging of stock solution with the first pipette and the washing of the second pipette can be effected substantially in parallel.

3. A system as in claim 1, further comprising a plurality of pipettes of differing capacities held by said supplying means.

4. A system as in claim 3, wherein said control means includes means for automatically selecting the first and second pipettes based on their respective capacities and the amounts of stock solutions to be taken therein.

5. A system as in claim 1, further comprising means for holding a plurality of the stock vessels at first separate predetermined locations and means for transferring said manipulating means with the selected pipette among said first predetermined locations.

6. A system as in claim 5, wherein said means for transferring said manipulating means is operative to transfer said manipulating means and the selected pipette to a position opposing said washing means, said pipette transferring means including means for releasing said manipulating means for the selected pipette and detachably connecting the selected pipette to the washing means with the means for transferring said manipulation means at said position opposing said washing means.

7. A system as in claim 5, further comprising means for holding the receptacles at second separate predetermined locations, said means for transferring said manipulating means being operative to transfer said manipulating means with the selected pipette among the second predetermined locations.

8. An automatic stock solution preparing and dispensing system, comprising:
    means for preparing stock solutions and storing the stock solutions in stock vessels;
    means for supplying a plurality of pipettes, each being manipulatable for taking stock solutions therein from the stock vessels and discharging the stock solutions therefrom into receptacles;
    means, detachably attachable to a selected pipette of the plurality of pipettes, for manipulating the selected pipette when detachably connected thereto so as to alternately take in the stock solution from different ones of the stock vessels and discharge the stock solution therein to the receptacles so as to prepare predetermined quantities of mixtures of stock solutions in the receptacles;
    said supplying means including means, detachably attachable to the selected pipette, for washing the selected pipette of remaining stock solution therein when detachably attached thereto after being manipulated by said manipulating means;
    pipette transferring means for transferring the selected pipette from said supplying means to said manipulating means so as to be detachably attached thereto and for transferring the selected pipette from said manipulating means to said washing means so as to be detachably attached thereto; and
    control means for controlling said preparing and storing means, said manipulating means, said washing means, and said pipette transferring means, said control means including:
        means for controlling said preparing and storing means such that the stock solutions are automatically prepared and stored in the stock vessels,
        means for automatically selecting a first pipette and a second pipette from said plurality of pipettes to be provided to said manipulating means, and
        transferring, manipulating and washing control means for controlling said pipette transferring means, said manipulating means and said washing means such that the first and second pipettes are in turn automatically successively transferred to said manipulating means, detachably attached to and manipulated by said manipulating means so as to take in the stock solution from the stock vessels and so as to discharge the stock solution therein to the receptacles, transferred to said washing means and washed by said washing means, and such that the first pipette is washed by said washing means while the second pipette is being manipulated by said manipulating means.

9. The system set forth in claim 8 wherein said control means controls said manipulating means, said transferring means, said washing means and said stock solution preparing and storing means in a time-division multiplex mode so that the preparing and taking in and discharging of stock solutions, and the washing of pipettes, can be effected substantially in parallel.

10. A system as in claim 8, wherein said preparing and storing means for detecting a shortage in the amount of stock solution in each of the stock vessels sufficient to make the predetermined quantities of the mixtures, raw material feeding means for feeding a raw material into a stock vessel to prepare the stock solution and means for measuring the amount of the raw material actually fed into the stock vessel, said means for controlling said stock solution preparing and storing means including shortage preparing means for preparing an amount of stock solution solution equal to the amount of any shortage detected by said detecting means so as to eliminate the shortage, said shortage preparing means including means for calculating the amount of the raw material in addition to that actually fed into the stock vessel measured by said measuring means and the amount of a diluent required to be additionally fed into the stock vessel in order to eliminate the shortage of the stock solution.

11. A system as in claim 8, wherein said means for controlling said preparing and storing means is operative substantially in parallel with operation of said transferring, manipulating and washing control means to prepare and store the stock solutions in the stock vessels simultaneously with operation of said manipulating means to prepare the mixtures in the receptacles.

12. A system as in claim 8, further comprising stock vessel holding means for holding a plurality of the stock vessels at separate predetermined locations and means transferring said manipulating means with the selected pipette among said predetermined locations.

13. A system as in claim 12, wherein said means for transferring said manipulating means is operative to transfer said manipulating means and the selected pipette to a position opposing said washing means, said pipette transferring means including means for releasing said manipulating means from the selected pipette and detachably attaching the selected pipette to the washing means with the means for transferring said manipulation means at said position opposing said washing means.

14. A system as in claim 13, wherein said preparing and storing means is spaced from said stock vessel holding means, said system further comprising means for transferring a selected one of said stock vessels between its predetermined location and said preparing and storing means, said preparing and storing means comprising means for storing a plurality of raw materials forming components of the stock solutions to be prepared and means, controlled by said means for controlling said preparing and storing means, for feeding predetermined amounts of the raw materials into the selected one of said stock vessels transferred thereto.

15. A system as in claim 1 or claim 8, wherein said washing means comprises means for providing a quantity of washing agent and drive means for driving the selected pipette detachably attached thereto so as to repeatedly take and discharge the washing agent into and from that pipette, said transferring, manipulating and washing control means being operative to control said drive means to take in and discharge the washing agent into and from the pipette a predetermined number of times in order to clean the pipette sufficiently for subsequent dispensing of stock solutions.

16. An automatic stock solution preparing and dispensing system, comprising:
   stock solution preparing means for preparing stock solutions and storing the stock solutions in stock vessels;
   dispensing means for dispensing predetermined amounts of different stock solutions from the stock vessels to receptacles to make a predetermined quantity of a mixture;
   means for detecting a shortage in the amount of stock solution in each of the stock vessels sufficient to make the predetermined quantity of the mixture; and
   control means for controlling said stock solution preparing means to prepare amounts of the stock solutions equal to the amounts of any shortages detected by said detecting means so as to eliminate the shortages.

17. A system as in claim 16, wherein said preparing and storing means includes raw material feeding means for feeding a raw material into a stock vessel to prepare a stock solution and means for measuring the amount of the raw material actually fed into the stock vessel, said control means including means for calculating the amount of the raw material in addition to that actually fed into the stock vessel measured by said measuring means and the amount of a diluent required to be additionally fed into the stock vessel in order to eliminate the shortage of the stock solution.

18. The system set forth in claim 16 wherein said control means controls said dispensing means and said stock solution preparing means in a time-division multiplex mode so that the preparation of stock solutions and the dispensation of stock solutions can be effected substantially simultaneously and in parallel with each other.

* * * * *